(12) United States Patent
Muratake et al.

(10) Patent No.: US 8,722,730 B2
(45) Date of Patent: May 13, 2014

(54) 5-MEMBERED HETEROCYCLIC COMPOUND

(75) Inventors: Hideaki Muratake, Tokyo (JP); Masayuki Noguchi, Chiba (JP); Koichi Shudo, Tokyo (JP)

(73) Assignee: Research Foundation Itsuu Laboratory, Tokyo (JP)

( * ) Notice: Subject to any disclaimer, the term of this patent is extended or adjusted under 35 U.S.C. 154(b) by 473 days.

(21) Appl. No.: 12/673,177

(22) PCT Filed: Aug. 14, 2008

(86) PCT No.: PCT/JP2008/064575
§ 371 (c)(1),
(2), (4) Date: May 12, 2010

(87) PCT Pub. No.: WO2009/022720
PCT Pub. Date: Feb. 19, 2009

(65) Prior Publication Data
US 2011/0213156 A1    Sep. 1, 2011

(30) Foreign Application Priority Data

Aug. 15, 2007 (JP) ................................ 2007-211649

(51) Int. Cl.
*A61K 31/341* (2006.01)
*C07D 307/40* (2006.01)

(52) U.S. Cl.
USPC ............................ 514/471; 549/487; 549/493

(58) Field of Classification Search
USPC .................................. 549/487, 493; 514/471
See application file for complete search history.

(56) References Cited

U.S. PATENT DOCUMENTS

| | | | |
|---|---|---|---|
| 5,977,108 A | 11/1999 | Kikuchi et al. | |
| 6,329,402 B1 | 12/2001 | Kikuchi et al. | |
| 6,541,474 B2 | 4/2003 | Kikuchi et al. | |
| 6,630,463 B2 | 10/2003 | Kikuchi et al. | |
| 6,884,808 B2 | 4/2005 | Kikuchi et al. | |

FOREIGN PATENT DOCUMENTS

| | | |
|---|---|---|
| JP | 61-022047 | 1/1986 |
| JP | 61-076440 | 4/1986 |
| JP | 9-071566 | 3/1997 |

OTHER PUBLICATIONS

Ettmayer et al. "Lessons Learned from Marketed and Investigational Prodrugs." J. Med. Chem., (2004), 47(10): 2393-2404.*
Stella, Valentino. "Prodrugs as therapeutics." Expert Opin. Ther. Patents (2004), 14(3): 277-280.*
Testa, Bernard. "Prodrug research: futile or fertile?" Biochemical Pharmacology, 68 (2004): 2097-2106.*
Balant ed in Wolff et al. Burger's Medicinal Chemistry and Drug Discovery. 5th ed. vol. 1: Principles and Practice. pp. 949-982.*
Balant ed in Wolkk ed Burger;'s Med. Chem. and Drug Discovery, 5th ed. vol. 1: Principles and Practice. pp. 949-982, 1997.*
Search report from E.P.O. that issued with respect to patent family member European Patent Application No. 08792455 9, mail date is Jul. 5, 2011.
U.S. Appl. No. 12/673,207 to Yohei Amano et al., which application is the National Stage of PCT/JP2008/064576, filed Aug. 14, 2008.
U.S. Appl. No. 12/673,221 to Yohei Amano et al., which application is the National Stage of PCT/JP2008/064577, filed Aug. 14, 2008.
Parnigotto et al., "Heterocyclic Derivatives of all-trans Retinoic Acid: in vitro Effects on Fibroblast/Keratinocyte Growth and Differentiation, and in vivo Effects on Guinea-Pig Skin," *Pharmacology & Toxicology* vol. 85, No. 2, pp. 49-55, compound 6, 1999.
Manfredini et al., "Retinoids as Potential Chemotherapeutic Agents. Synthesis, Cytostatic, and Differentiating Activities of New Heterocyclic Analogues of Retinoic," *Medicinal Chemistry Research* vol. 8, No. 6, pp. 291-304, compound 16a, b, d, 1998.
International Search Report that issued with respect to PCT/JP2008/064575, mailed Sep. 30, 2008.
International Preliminary Report on Patentability, including the Written Opinion (in English) that issued with respect to PCT/JP2008/064575, mailed Feb. 25, 2010.

* cited by examiner

*Primary Examiner* — Patricia L Morris
(74) *Attorney, Agent, or Firm* — Greenblum & Bernstein, P.L.C.

(57) ABSTRACT

A compound represented by the following general formula (I):

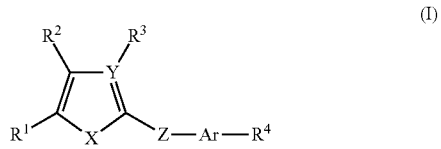

[wherein $R^1$ and $R^2$ represent an alkyl group, X represents —S—, —O— or —NH—, Y represents C or N, $R^3$ represents hydrogen atom or a $C_{1-10}$ alkyl group, Z represents —CO—N($R^5$)— ($R^5$ represents hydrogen atom or a $C_{1-6}$ alkyl group) or —C($R^6$)=C($R^7$)—CO—NH— ($R^6$ and $R^7$ represent hydrogen atom or a $C_{1-6}$ alkyl group), Ar represents an aryldiyl group or a heteroaryldiyl group, and $R^4$ represents —COOH, —OCH$_2$—COOH, —CH$_2$—COOH, or —CH$_2$—CH$_2$—COOH], which has a retinoid action and is useful as an active ingredient of a medicament.

6 Claims, No Drawings

5-MEMBERED HETEROCYCLIC COMPOUND

TECHNICAL FIELD

The present invention relates to a 5-membered heterocyclic compound having a retinoid action.

BACKGROUND ART

Retinoic acid (vitamin A acid), an active metabolite of vitamin A, has extremely important physiological functions, e.g., inducing differentiation of immature cells under development processes toward mature cells having specific functions, enhancement of cell proliferation, life support action, and the like. Retinoic acid and compounds having retinoic acid-like biological activities are collectively referred to as "retinoids".

It has been proved that all-trans retinoic acid, considered as a biological retinoid, regulates proliferation and differentiation of animal cells, cellular mortalities, and the like. It has also been revealed that various vitamin A derivatives synthesized so far also have similar physiological functions, for example, the benzoic acid derivatives disclosed in Japanese Patent Unexamined Publication (KOKAI) Nos. 61-22047 and 61-76440, the compounds described in Journal of Medicinal Chemistry, 31 (11), 2182, 1988, and the like. Furthermore, various synthetic retinoids are exemplified in Adv. Drug Res., 24, 81, 1993 and J. Med. Chem., 48, 5875, 2005. For example, it is suggested that 4-[(5,6,7,8-tetrahydro-5,5, 8,8-tetramethyl-2-naphthalenyl)carbamoyl]benzoic acid (Am80) also exhibits physiological actions similar to (but different from) those of retinoic acid (Cell Structure Funct., 16, 113, 1991; Biochem. Biophys. Res. Com., 166, 1300, 1990). Besides these, it has been demonstrated that various compounds have retinoic acid-like activity, such as the heterocyclic ring-containing carboxylic acid derivatives (Japanese Patent Unexamined Publication No. 9-71566).

For retinoids, various pre-clinical and clinical researches have been conducted for use of them as a medicament for therapeutic or prophylactic treatment of skin diseases, autoimmune diseases, lipid or sugar metabolic disorders, cranial nerve diseases, and malignant tumors. For example, it has been found that they are useful for therapeutic or prophylactic treatment of hyperkaratosis of epithelial tissue, rheumatism, delayed allergy, multiple sclerosis, autoimmune diseases, bone diseases, leukemia, certain types of cancers and cranial nerve diseases, spinal cord injury, cardiovascular diseases such as arteriosclerosis, vasoconstriction or restenosis, and control of neovascularization, diabetes, and disorder of lipid metabolism. As described above, retinoids are characterized by having various biological activities and pharmacological activities, and thus being applicable to various diseases as objects of therapeutic treatment. However, it cannot necessarily be considered that they are practically used as satisfactory medicaments in view of selectivity for the action and action site, kinetics in the living bodies such as that for absorption and excretion, and side reactions, because of such diversity as described above.

Therefore, retinoids exhibiting limited actions, or those showing metabolism, absorption, excretion, and distribution suitable for a specific object of therapeutic treatment are desired. For example, for internal diseases, a retinoid showing less action on the skin is preferred, and for the skin, a retinoid having characteristics suitable for external preparations is desired. Further, for chronic diseases, a retinoid compound showing prolonged action is preferred, for various kinds of cancers, a retinoid which acts on dividing cells such as cancer cells at an optimum concentration different from that for non-dividing cells is preferred, and for cranial nerve diseases, a retinoid having high permeability for the blood-brain barrier, and superior distribution in cranial nerves is desired. Moreover, a retinoid showing less side reactions is desirable as a medicament.

From a viewpoint of chemical compounds, the tert-butyl-substituted furancarboxylic acid derivatives and tert-butyl-substituted thiophenecarboxylic acid derivatives described in Med. Chem. Res., 8, 291, 1998 have been reported as compounds having a structure similar to that of the compounds of the present invention (page 294, Compounds 16a and 16d). However, these compounds have only a weak differentiation-inducing action on the human acute promyelocytic leukemia cell strain HL-60, and thus have extremely weak actions as retinoids.

Non-patent document 1: Med. Chem. Res., 8, 291, 1998
Disclosure of the Invention

DISCLOSURE OF THE INVENTION

Object to be Achieved by the Invention

An object of the present invention is to provide a novel compound having a retinoid action and useful as an active ingredient of a medicament.

Means for Achieving the Object

The inventors of the present invention conducted various researches in order to achieve the aforementioned object, and as a result, found that the compounds represented by the following general formula had a desired retinoid action. The present invention was accomplished on the basis of the aforementioned finding.

The present invention thus provides a compound represented by the following general formula (I):

[Formula 1]

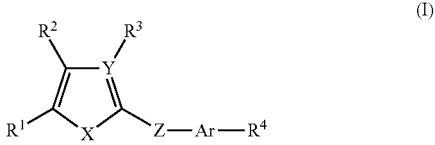

[wherein $R^1$ and $R^2$ independently represent a $C_{3-10}$ alkyl group (the alkyl group may have a substituent), X represents —S—, —O— or —NH—, Y represents C or N, $R^3$ represents hydrogen atom or a $C_{1-10}$ alkyl group (the alkyl group may have a substituent), Z represents —CO—N($R^5$)— ($R^5$ represents hydrogen atom or a $C_{1-6}$ alkyl group) or —C($R^6$)═C ($R^7$)—CO—NH— ($R^6$ and $R^7$ independently represent hydrogen atom or a $C_{1-6}$ alkyl group), Ar represents an aryldiyl group or a heteroaryldiyl group (the aryldiyl group and the heteroaryldiyl group may have a substituent), and $R^4$ represents —COOH, —OCH$_2$—COOH, —CH$_2$—COOH, or —CH$_2$—CH$_2$—COOH], a salt thereof, or an ester thereof.

According to a preferred embodiment of the aforementioned invention, there is provided the aforementioned compound represented by the general formula (I), a salt thereof, or an ester thereof, wherein $R^1$ and $R^2$ represent isopropyl group, X is —S—, —O—, or —NH—, Y is C, $R^3$ is hydrogen atom or a $C_{1-10}$ alkyl group, Z is —CO—NH—, —CH═CH—

CO—NH—, or —C(CH$_3$)=CH—CO—NH—, Ar is a phenylene group, a pyridinediyl group, or a thiophenediyl group (these groups may be substituted with one or two the same or different substituents selected from a halogen atom, hydroxyl group, an alkoxy group, and an alkyl group), and R$^4$ is —COOH, —OCH$_2$—COOH, —CH$_2$—COOH, or —CH$_2$—CH$_2$—COOH.

From another aspect of the present invention, there is provided a medicament comprising a compound represented by the aforementioned general formula (I), a physiologically acceptable salt thereof, or an ester thereof. This medicament can be used as an agent having a retinoid action.

The present invention further provides use of a compound represented by the aforementioned general formula (I), a physiologically acceptable salt thereof, or an ester thereof for manufacture of the aforementioned medicament, and a method for prophylactic and/or therapeutic treatment of a disease preventable and/or curable by administration of a retinoid, which comprises the step of administering an effective amount of a compound represented by the aforementioned general formula (I), a physiologically acceptable salt thereof, or an ester thereof to a mammal including human.

BEST MODE FOR CARRYING OUT THE INVENTION

In the specification, the alkyl group may be any of a linear alkyl group, a branched alkyl group, a cyclic alkyl group, and an alkyl group consisting of a combination these. The same shall apply to an alkyl moiety of other substituents having the alkyl moiety (alkoxyl group and the like).

When the alkyl group has a substituent, type, substituting position, and number of the substituent are not particularly limited. Examples of the substituent include, for example, a halogen atom (fluorine atom, chlorine atom, bromine atom, or iodine atom), hydroxyl group, an alkoxy group, amino group, oxo group, and the like, but the substituent is not limited to these examples.

As the C$_{3-10}$ alkyl group represented by R$^1$ or R$^2$, a linear or branched alkyl group is preferred, it is more preferred that R$^1$ and R$^2$ both represent a C$_{3-6}$ branched alkyl group, and it is particularly preferred that R$^1$ and R$^2$ both represent isopropyl group.

X represents —S—, —O—, or —NH—, Y represents C or N, and it is preferred that X is —S—, —O—, or —NH—, and Y is C. As X, —O— is preferred.

R$^3$ represents hydrogen atom or a C$_{1-10}$ alkyl group, it is preferably hydrogen atom or a C$_{1-6}$ alkyl group, it is more preferably hydrogen atom or a branched C$_{1-6}$ alkyl group, and it is particularly preferably hydrogen atom. It is preferred that X is —O—, and Y is C, and in this case, it is more preferred that R$^3$ is hydrogen atom.

Z is preferably —CO—NH— or —C(R$^6$)=CH—CO—NH— (R$^6$ represents hydrogen atom or a C$_{1-6}$ alkyl group), more preferably —CO—NH—.

The aryl ring constituting the aryldiyl group represented by Ar may be a monocyclic aryl ring or a condensed aryl ring, and a 6- to 14-membered aryl ring can be used. More specifically, examples include, for example, benzene ring, naphthalene ring, and the like. As the aryl ring, benzene ring is preferred. The binding positions of the aryldiyl group are not particularly limited, and it may binds at positions at which it can bind. For example, in the case of phenylene group, said group may be any of 1,2-phenylene group, 1,3-phenylene group, and 1,4-phenylene group.

Although type and number of heteroatoms contained in the heteroaryl ring constituting the heteroaryldiyl group represented by Ar are not particularly limited, a heteroaryl ring containing one or more heteroatoms selected from the group consisting of nitrogen atom, oxygen atom and sulfur atom as ring-constituting atoms is preferred. When two or more heteroatoms are contained, they may be the same or different. The heteroaryl ring may be a monocyclic heteroaryl ring or a condensed heteroaryl ring. More specifically, examples include, for example, pyridine ring, pyrimidine ring, pyrazine ring, pyridazine ring, triazine ring, quinoline ring, isoquinoline ring, quinazoline ring, phthalazine ring, quinoxaline ring, naphthylidine ring, cinnoline ring, thiophene ring, furan ring, pyrrole ring, imidazole ring, pyrazole ring, triazole ring, tetrazole ring, oxazole ring, thiazole ring, benzothiazole ring, benzofuran ring, indole ring, indazole ring, benzimidazole ring, benzotriazole ring, benzoxazole ring, purine ring, and the like, but the heteroaryl ring is not limited to these examples. Among them, pyridine ring is preferred. The binding positions of the heteroaryldiyl group are not particularly limited, and said group can bind at arbitrary positions at which it can bind. For example, in the case of pyridinediyl group, said group may be any of 2,3-pyridinediyl group, 2,4-pyridinediyl group, 2,5-pyridinediyl group, and 2,6-pyridinediyl group.

The aryldiyl group and heteroaryldiyl group represented by Ar may have a substituent. Examples of the substituent include, for example, an alkyl group, a halogen atom (fluorine atom, chlorine atom or the like), hydroxyl group, an alkoxyl group, and the like, but the substituent is not limited to these examples. For example, examples include, but not limited to, monofluorophenylene group, difluorophenylene group, monochlorophenylene group, methoxyphenylene group, hydroxyphenylene group, monofluoropyridinediyl group, monochloropyridinediyl group, and the like.

R$^4$ represents —COOH, —OCH$_2$—COOH, —CH$_2$—COOH, or —CH$_2$—CH$_2$—COOH, and it is preferably —COOH.

The compounds of the present invention represented by the general formula (I) may exist in the forms of acid addition salts or base addition salts, and any of such salts also fall within the scope of the present invention. Examples of the acid addition salts include mineral acid salts such as hydrochloride or hydrobromide, and organic acid salts such as p-toluenesulfonate, methanesulfonate, oxalate, or tartrate. As the base addition salts, metal salts such as, for example, sodium salt, potassium salt, magnesium salt, or calcium salt, ammonium salts, or organic amine salts such as triethylamine salt or ethanolamine salt, and the like may be used. Further, the compounds may exist in the forms of amino acid salts such as glycine salt.

As the ester of the compound of the present invention represented by general formula (I), a physiologically acceptable ester is preferred. Specific examples of preferred residues forming the ester include, for example, methyl group, ethyl group, propyl group, isopropyl group, butyl group, isobutyl group, t-butyl group, benzyl group, acetoxymethyl group, 1-(acetoxy)ethyl group, propionyloxymethyl group, 1-(propionyloxy)ethyl group, butyryloxymethyl group, 1-(butyryloxy)ethyl group, isobutylyloxymethyl group, 1-(isobutyryloxy)ethyl group, valeryloxymethyl group, 1-(valeryloxy)ethyl group, isovaleryloxymethyl group, 1-(isovaleryloxy)ethyl group, pivaloyloxymethyl group, 1-(pivaloyloxy)ethyl group, methoxycarbonyloxymethyl group, 1-(methoxycarbonyloxy)ethyl group, ethoxycarbonyloxymethyl group, 1-(ethoxycarbonyloxy)ethyl group, propoxycarbonyloxymethyl group, 1-(propoxycarbonyloxy)ethyl group, isopropoxycarbonyloxymethyl group, 1-(isopropoxycarbonyloxy)ethyl group, butoxycarbonyloxymethyl group, 1-(buthoxycarbonyloxy)ethyl group, isobutoxycarbonyloxymethyl group, 1-(isobuthoxycarbonyloxy)ethyl group, t-buthoxycarbonyloxymethyl group, 1-(t-buthoxycarbonyloxy)ethyl group, cyclopentanecarbonyloxymethyl group, 1-(cyclopentanecarbonyloxy)ethyl group, cyclohexanecarbonyloxymethyl group, 1-(cyclohexanecarbonyloxy)ethyl group, cyclopenthyloxycarbonyloxymethyl group, 1-(cyclopenthyloxycarbonyloxy)ethyl group, cyclohexyloxycarbonyloxymethyl group, 1-(cyclohexyloxycarbonyloxy)ethyl group, benzoyloxymethyl group, 1-(benzoyloxy)ethyl group, phenoxycarbonyloxymethyl group, 1-(phenoxycarbonyloxy)ethyl group, (5-methyl-2-oxo-1,3-dioxoren-4-yl)methyl group, 2-trimethylsilylethyl group, and the like, but the examples are not limited to these examples.

The compounds of the present invention may have one or more asymmetric carbon atoms depending on types of substituents. Arbitrary optical isomers based on these asymmetric carbon atoms, arbitrary mixtures of optical isomers, racemates, diastereomers based on two or more asymmetric carbon atoms, arbitrary mixtures of diastereomers, and the like all fall within the scope of the present invention. Further, arbitrary hydrates or solvates of the compounds in free form or in the form of a salt also fall within the scope of the present invention.

The preparation methods of preferred compounds among the compounds of the aforementioned formula (I) are specifically described in the examples given in the present specification. Therefore, any compounds falling within the scope of the present invention can be prepared by suitably selecting starting materials, reaction regents, reaction conditions and the like used in those preparation methods, and if necessary, appropriately modifying or altering the preparation methods. However, the preparation methods of the compounds of the present invention are not limited to those specifically explained in the examples.

The compounds represented by the aforementioned general formula (I) and salts thereof have retinoid-like physiological activities (typical examples include cell differentiating activity, cell proliferation enhancing activity, life supporting activity and the like). Therefore, a medicament comprising a compound represented by general formula (I) or a physiologically acceptable salt thereof as an active ingredient is useful as an agent having a retinoid action. The medicament of the present invention containing the aforementioned active ingredient has, for example, cell differentiating activity, cell proliferation enhancing activity, life supporting activity and the like, and it can be used for prophylactic and/or therapeutic treatment of vitamin A deficiency disease, hyperkeratosis of epithelial tissue, psoriasis, allergic diseases, immunological diseases such as rheumatism, bone diseases, diabetes mellitus, leukemia, or cancers. Moreover, a medicament containing an ester of a compound represented by general formula (I) as an active ingredient can be used as a medicament containing a prodrug of the compound represented by general formula (I).

The medicament of the present invention comprises, as an active ingredient, one or more kinds of substances selected from the group consisting of the compounds represented by the aforementioned general formula (I), physiologically acceptable salts thereof, and esters thereof. As the medicament of the present invention, the aforementioned substance, per se, may be administered. However, a pharmaceutical composition for oral administration or parenteral administration may preferably be administered which can be prepared by a method well known to those skilled in the art. Examples of the pharmaceutical compositions suitable for oral administrations include, for example, tablets, capsules, powders, subtilized granules, granules, liquids, syrups and the like. Examples of the pharmaceutical compositions suitable for parenteral administrations include, for example, injections, drops, suppositories, inhalants, eye drops, nasal drops, ointments, creams, patches, transdermal preparations, transmucosal preparations, and the like.

Examples of pharmaceutically acceptable additives used for preparation of the aforementioned pharmaceutical compositions include, for example, excipients, disintegrators and disintegrating aids, binders, lubricants, coating agents, colorants, diluents, base materials, dissolving agents and dissolving aids, isotonic agents, pH modifiers, stabilizers, propellants, adhesives and the like. They can be suitably selected by those skilled in the art depending on the form of the pharmaceutical composition, and two or more kinds of them may be used in combination. The aforementioned pharmaceutical composition may be further added with one or more kinds of active ingredients such as retinoids.

EXAMPLES

Hereafter, the present invention will be more specifically explained with reference to examples. However, the scope of the present invention is not limited to the following examples. In the following examples, Me represents methyl group, Et represents ethyl group, Ac represents acetyl group, and AcOEt represents ethyl acetate.

Example 1

4,5-Diisopropylfuran-2-carboxylic acid

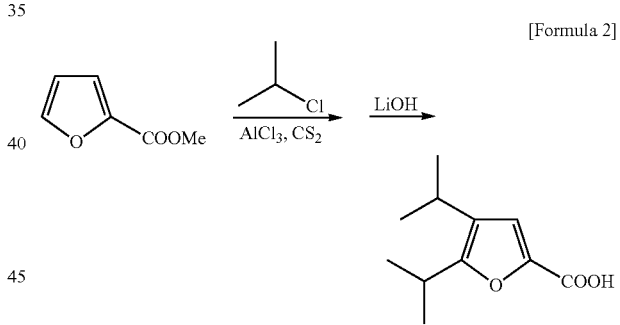

[Formula 2]

A suspension of methyl furan-2-carboxylate (21.4 g, 0.17 mol) and anhydrous aluminum chloride (40.0 g, 0.300 mol) in carbon disulfide (400 ml) was slowly added with 2-chloropropane (5.0 ml, 54.7 mmol) at room temperature, and the mixture was vigorously stirred for 15 minutes. The reaction mixture was further added dropwise with 2-chloropropane (34.0 ml, 0.372 mol) over 2 hours or more, and then the mixture was stirred at room temperature for 3 days. The reaction mixture was poured into ice water, and the insoluble matter was removed by filtration through Celite. The filtrate was extracted with chloroform, and then the organic layer was washed with saturated aqueous sodium hydrogencarbonate. The reaction mixture was treated in a conventional manner, and then the residue was distilled to obtain methyl 4,5-diisopropylfuran-2-carboxylate as pale yellow oil (17.12 g, 48%).
Bp: 80-91° C./0.8 mmHg
$^1$H-NMR (CDCl$_3$) δ: 1.16 (6H, d, J=7 Hz), 1.28 (6H, d, J=7 Hz), 2.83 (1H, sep, J=7 Hz), 3.07 (1H, sep, J=7 Hz), 3.85 (3H, s), 7.07 (1H, s)

A solution of the aforementioned compound (6.43 g, 30.6 mmol) in methanol-1,2-dimethoxyethane-water (3:2:1, 24 ml) was added with lithium hydroxide monohydrate (1.93 g, 46.0 mmol), and the mixture was stirred at room temperature for 5 hours. The reaction mixture was cooled on ice, and then added with aqueous hydrochloric acid (2 N, 23 ml, 46 mmol), and the mixture was extracted with ethyl acetate. The reaction mixture was treated in a conventional manner, and then the resultant was recrystallized from hexane to obtain the title compound as colorless prisms (5.45 g, 91%, 44% overall).

Mp: 105-106° C.

$^1$H-NMR (CDCl$_3$) δ: 1.18 (6H, d, J=7 Hz), 1.30 (6H, d, J=7 Hz), 2.85 (1H, sep, J=7 Hz), 3.10 (1H, sep, J=7 Hz), 7.21 (1H, s), 10.31 (1H, br s, COOH)

Example 2

4-[(4,5-Diisopropylfuran-2-carbonyl)amino]benzoic acid (1)

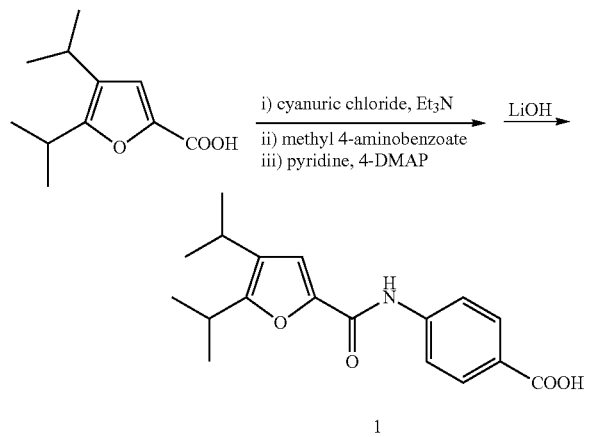

A solution of 4,5-diisopropylfuran-2-carboxylic acid (50 mg, 0.255 mmol) and cyanuric chloride (71 mg, 0.385 mmol) in acetone (3 ml) was added with triethylamine (142 μl, 1.021 mmol), and the mixture was stirred at room temperature for 3.5 hours. The reaction mixture was added with methyl 4-aminobenzoate (77 mg, 0.510 mmol), and the mixture was further stirred for 14 hours. The reaction solvent was evaporated, then the residue was dissolved in pyridine (1 ml), the solution was added with 4-dimethylaminopyridine (1 mg, 8.20 μmol), and the mixture was stirred at room temperature for 4 hours. Pyridine was evaporated, and then the reaction mixture was dissolved in 10% methanol-chloroform, the solution was added with silica gel (1.0 g), and the mixture was evaporated to dryness. The residue was purified by silica gel chromatography [hexane-ethyl acetate (6:1)] to obtain methyl 4-[(4,5-diisopropylfuran-2-carbonyl)amino]benzoate (75 mg, 89%) as colorless prisms.

Mp: 198-200° C. (CH$_2$Cl$_2$-hexane)

MS (m/z): 329 (M$^+$, 21), 314 (6), 298 (2), 179 (100), 91 (9), 77 (6), 43 (12), 41 (10)

IR (KBr) cm$^{-1}$: 1694, 1663, 1596

$^1$H-NMR (CDCl$_3$) δ: 1.18 (6H, d, J=7 Hz), 1.31 (6H, d, J=7 Hz), 2.84 (1H, sep, J=7 Hz), 3.12 (1H, sep, J=7 Hz), 3.91 (3H, s), 7.16 (1H, s), 7.74 (2H, A$_2$B$_2$, J=8.5 Hz), 8.04 (2H, A$_2$B$_2$, J=8.5 Hz), ca. 8.06 (1H, br s, CONH)

The aforementioned methyl ester (60 mg, 0.182 mmol) was dissolved in methanol-1,2-dimethoxyethane-water (3:2:1, 3 ml), the solution was added with lithium hydroxide monohydrate (12 mg, 0.286 mmol), and the mixture was refluxed by heating for 1 hour with stirring. The reaction mixture was cooled on ice, and then added with aqueous hydrochloric acid (1 N, 286 μl, 286 μmol), and the mixture was extracted with ethyl acetate. The residue was recrystallized to obtain the title compound (1, 55 mg, 96%, 85% overall) as colorless prisms.

Mp: 120-121° C. and 177.5-179.5° C. (CH$_2$Cl$_2$)

MS (m/z): 315 (M$^+$, 23), 300 (6), 270 (1), 179 (100), 108 (4), 93 (5), 91 (7), 77 (6), 65 (9), 43 (11), 41 (9)

IR (KBr) cm$^-$: 1689, 1646

$^1$H-NMR (CDCl$_3$) δ: 1.19 (6H, d, J=7 Hz), 1.32 (6H, d, J=7 Hz), 2.85 (1H, sep, J=7 Hz), 3.13 (1H, sep, J=7 Hz), 7.18 (1H, s), 7.78 (2H, A$_2$B$_2$, J=8.5 Hz), 8.07 (1H, br s, CONH), 8.12 (2H, A$_2$B$_2$, J=8.5 Hz).

Example 3

4-[(4,5-Diisopropylfuran-2-carbonyl)methylamino] benzoic acid (2)

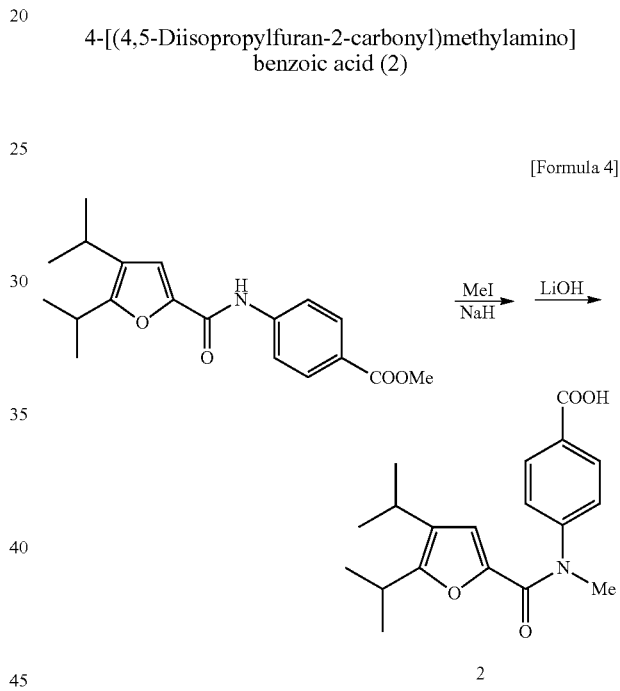

A solution of methyl 4-[(4,5-diisopropylfuran-2-carbonyl)amino]benzoate (60 mg, 0.182 mmol) obtained above and iodomethane (57 μl, 0.915 mmol) in anhydrous tetrahydrofuran (4 ml) was cooled on ice, and added with sodium hydride (60% mineral oil dispersion, 22 mg, 0.550 mmol), and the mixture was stirred under an argon atmosphere for 15 minutes, and at room temperature for further 30 minutes. The reaction mixture was added with saturated aqueous ammonium chloride, and the mixture was extracted with chloroform. The reaction mixture was treated in a conventional manner, and then the resultant was purified by silica gel chromatography [chloroform-hexane (4:1)] to obtain methyl 4-[(4,5-diisopropylfuran-2-carbonyl)methylamino]benzoate (60 mg, 96%) as colorless vitrified substance.

MS (m/z): 343 (M$^+$, 14), 328 (5), 300 (8), 273 (6), 179 (100), 108 (9), 91 (9), 77 (12), 43 (22), 41 (14)

IR (neat) cm$^{-1}$: 1718, 1636, 1597

$^1$H-NMR (CDCl$_3$) δ: 0.78 (6H, d, J=7 Hz), 1.07 (6H, d, J=7 Hz), 2.68 (1H, sep, J=7 Hz), 2.78 (1H, sep, J=7 Hz), 3.43 (3H, s), 3.93 (3H, s), 6.80 (1H, s), 7.23 (2H, A$_2$B$_2$, J=8 Hz), 8.04 (2H, A$_2$B$_2$, J=8 Hz)

The aforementioned methyl ester (58 mg, 0.169 mmol) was hydrolyzed in the same manner as that of Example 2, and the residue was recrystallized to obtain the title compound (2, 52 mg, 93%, 89% overall) as colorless prisms.

Mp: 184-186° C. (CH$_2$Cl$_2$-hexane)

MS (m/z): 329 (M$^+$, 14), 314 (5), 286 (6), 258 (4), 179 (100), 108 (8), 93 (8), 91 (9), 77 (11), 65 (14), 43 (22), 41 (15)

IR (KBr) cm$^{-1}$: 1708, 1579

$^1$H-NMR (CDCl$_3$) δ: 0.79 (6H, d, J=7 Hz), 1.08 (6H, d, J=7 Hz), 2.68 (1H, sep, J=7 Hz), 2.79 (1H, sep, J=7 Hz), 3.46 (3H, s), 6.85 (1H, s), 7.27 (2H, A$_2$B$_2$, J=8.5 Hz), 8.12 (2H, A$_2$B$_2$, J=8.5 Hz).

Example 4

4-[(4,5-Diisopropylfuran-2-carbonyl)amino]phenyloxyacetic acid (3)

[Formula 5]

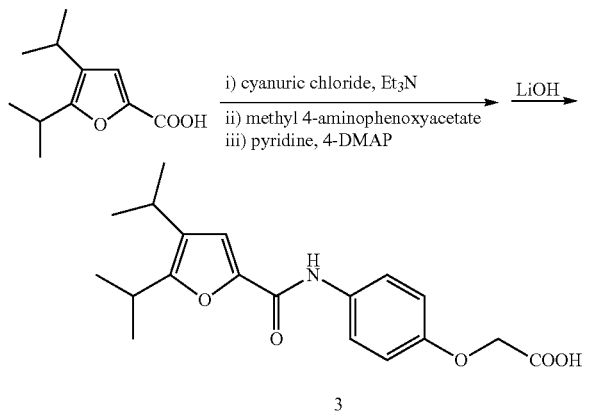

In the same manner as that of Example 2, 4,5-diisopropylfuran-2-carboxylic acid (60 mg, 0.306 mmol) was condensed with methyl 4-aminophenoxyacetate, and the resultant was purified by silica gel chromatography (0.5% methanol-chloroform) to obtain methyl 4-[(4,5-diisopropylfuran-2-carbonyl)amino]phenyloxyacetate (94 mg, 86%) as colorless needles.

Mp: 104-105° C. (CH$_2$Cl$_2$-hexane)

MS (m/z): 359 (M$^+$, 34), 344 (3), 179 (100), 108 (7), 93 (8), 91 (9), 59 (8), 45 (16), 43 (14), 41 (12)

IR (KBr) cm$^{-1}$: 1759, 1646, 1603

$^1$H-NMR (CDCl$_3$) δ: 1.17 (6H, d, J=7 Hz), 1.30 (6H, d, J=7 Hz), 2.83 (1H, sep, J=7 Hz), 3.10 (1H, sep, J=7 Hz), 3.82 (3H, s), 4.64 (2H, s), 2.04-2.11 (1H, m), 6.92 (2H, A$_2$B$_2$, J=9 Hz), 7.11 (1H, s), 7.56 (2H, A$_2$B$_2$, J=9 Hz), 7.84 (1H, br s, CONH)

The aforementioned methyl ester (63 mg, 0.175 mmol) was hydrolyzed in the same manner as that of Example 2, and the residue was recrystallized to obtain the title compound (3, 59 mg, 97%, 83% overall) as colorless needles.

Mp: 83-85° C. (CH$_2$Cl$_2$-hexane)

MS (m/z): 345 (M$^+$, 27), 330 (4), 179 (100), 108 (13), 43 (16), 41 (12)

IR (KBr) cm$^{-1}$: 1746, 1616

$^1$H-NMR (CDCl$_3$) δ: 1.17 (6H, d, J=7 Hz), 1.30 (6H, d, J=7 Hz), 2.83 (1H, sep, J=7 Hz), 3.11 (1H, sep, J=7 Hz), 4.67 (2H, s), 6.93 (2H, A$_2$B$_2$, J=9 Hz), 7.12 (1H, s), 7.57 (2H, A$_2$B$_2$, J=9 Hz), 7.85 (1H, br s, CONH)

Example 5

4-[(4,5-Diisopropylfuran-2-carbonyl)amino]phenylacetic acid (4)

[Formula 6]

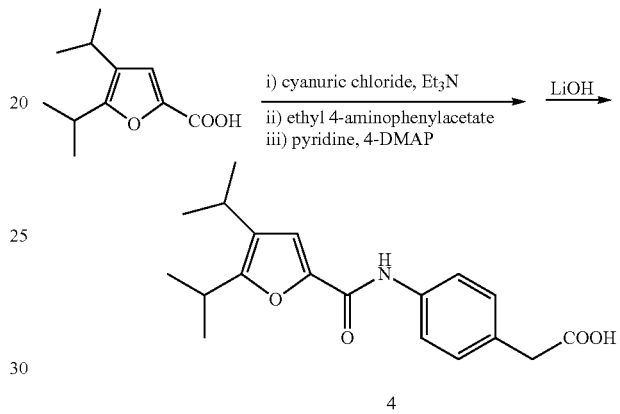

In the same manner as that of Example 2, 4,5-diisopropylfuran-2-carboxylic acid (60 mg, 0.306 mmol) was condensed with ethyl 4-aminophenylacetate, and the resultant was purified by silica gel chromatography [hexane-ethyl acetate (4:1)] to obtain ethyl 4-[(4,5-diisopropylfuran-2-carbonyl)amino]phenylacetate (94 mg, 86%) as colorless needles.

Mp: 91.5-92.5° C. (CH$_2$Cl$_2$-hexane)

MS (m/z): 357 (M$^+$, 27), 342 (5), 284 (9), 179 (100), 108 (8), 77 (9), 43 (15), 41 (11)

IR (KBr) cm$^{-1}$: 1736, 1642, 1606, 1595

$^1$H-NMR (CDCl$_3$) δ: 1.17 (6H, d, J=7 Hz), 1.25 (3H, t, J=7 Hz), 1.31 (6H, d, J=7 Hz), 2.84 (1H, sep, J=7 Hz), 3.11 (1H, sep, J=7 Hz), 3.59 (2H, s), 4.15 (2H, q, J=7 Hz), 7.12 (1H, s), 7.28 (2H, A$_2$B$_2$, J=8.5 Hz), 7.60 (2H, A$_2$B$_2$, J=8.5 Hz), 7.88 (1H, br s, CONH)

The aforementioned ethyl ester (70 mg, 0.196 mmol) was hydrolyzed in the same manner as that of Example 2, and the residue was recrystallized to obtain the title compound (4, 64 mg, 99%, 85% overall) as colorless needles.

Mp: 154-156° C. (CH$_2$Cl$_2$-hexane)

MS (m/z): 329 (M$^+$, 23), 314 (7), 179 (100), 77 (10), 43 (15), 41 (11)

IR (KBr) cm$^{-1}$: 1718, 1643

$^1$H-NMR (CDCl$_3$) δ: 1.17 (6H, d, J=7 Hz), 1.31 (6H, d, J=7 Hz), 2.84 (1H, sep, J=7 Hz), 3.11 (1H, sep, J=7 Hz), 3.64 (2H, s), 7.13 (1H, s), 7.28 (2H, A$_2$B$_2$, J=8.5 Hz), 7.62 (2H, A$_2$B$_2$, J=8.5 Hz), 7.88 (1H, br s, CONH)

Example 6

3-[(4,5-Diisopropylfuran-2-carbonyl)amino]benzoic acid (5)

[Formula 7]

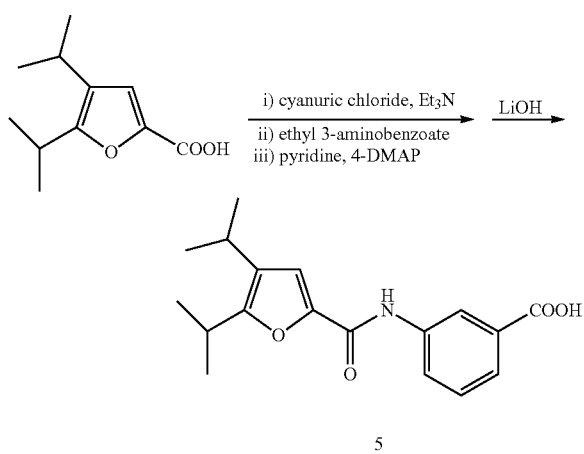

In the same manner as that of Example 2, 4,5-diisopropylfuran-2-carboxylic acid (60 mg, 0.306 mmol) was condensed with ethyl 3-aminobenzoate, and the resultant was purified by silica gel chromatography [hexane-ethyl acetate (7:2)] to obtain ethyl 3-[(4,5-diisopropylfuran-2-carbonyl)amino]benzoate (93 mg, 89%) as colorless needles.

Mp: 144-145° C. ($CH_2Cl_2$-hexane)
MS (m/z): 343 ($M^+$, 37), 328 (4), 298 (5), 179 (100), 91 (11), 43 (18), 41 (12)
IR (KBr) $cm^{-1}$: 1717, 1648, 1606
$^1$H-NMR ($CDCl_3$) δ: 1.18 (6H, d, J=7 Hz), 1.32 (6H, d, J=7 Hz), 1.41 (3H, t, J=7 Hz), 2.85 (1H, sep, J=7 Hz), 3.12 (1H, sep, J=7 Hz), 4.40 (2H, q, J=7 Hz), 7.15 (1H, s), 7.45 (1H, dd, J=8, 7.5 Hz), 7.81 (1H, ddd, J=7.5, 1.5, 1 Hz), 7.99 (1H, br s, CONH), 8.06 (1H, dd, J=2.5, 1.5 Hz), 8.12 (1H, ddd, J=8, 2.5, 1 Hz)

The aforementioned ethyl ester (61 mg, 0.178 mmol) was hydrolyzed in the same manner as that of Example 2, and the residue was recrystallized to obtain the title compound (5, 52 mg, 93%, 83% overall) as colorless prisms.

Mp: 243.5-245° C. (MeOH—$CH_2Cl_2$)
MS (m/z): 315 ($M^+$, 28), 300 (7), 179 (100), 91 (9), 77 (8), 65 (13), 43 (16), 41 (13)
IR (KBr) $cm^{-1}$: 1701, 1630, 1608
$^1$H-NMR ($CDCl_3$) δ: 1.19 (6H, d, J=7 Hz), 1.33 (6H, d, J=7 Hz), 2.85 (1H, sep, J=7 Hz), 3.13 (1H, sep, J=7 Hz), 7.17 (1H, s), 7.49 (1H, dd, J=8, 7.5 Hz), 7.87 (1H, ddd, J=7.5, 1.5, 1 Hz), 8.01 (1H, br s, CONH), 8.11 (1H, dd, J=2, 1.5 Hz), 8.21 (1H, ddd, J=8, 2, 1 Hz).

Example 7

3-[4-[(4,5-Diisopropylfuran-2-carbonyl)amino]phenyl]propionic acid (6)

[Formula 8]

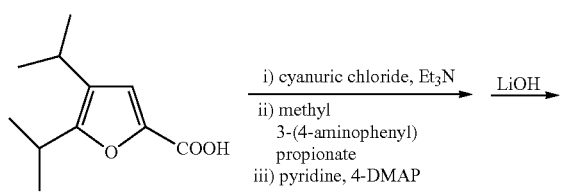

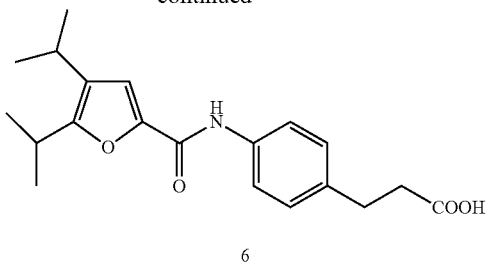

In the same manner as that of Example 2, 4,5-diisopropylfuran-2-carboxylic acid (90 mg, 0.459 mmol) was condensed with methyl 3-[4-aminophenyl]propionate, and the resultant was purified by silica gel chromatography [benzene-ethyl acetate (14:1)] to obtain methyl 3-[4-[(4,5-diisopropylfuran-2-carbonyl)amino]phenyl]propionate (138 mg, 84%) as colorless needles.

Mp: 93-94° C. ($CH_2Cl_2$-hexane)
MS (m/z): 357 ($M^+$, 30), 284 (7), 179 (100), 118 (7), 108 (7), 91 (9), 77 (7), 43 (11), 41 (8)
IR (KBr) $cm^{-1}$: 1731, 1642
$^1$H-NMR ($CDCl_3$) δ: 1.17 (6H, d, J=7 Hz), 1.31 (6H, d, J=7 Hz), 2.63 (2H, t, J=7.5 Hz), 2.84 (1H, sep, J=7 Hz), 2.94 (2H, t, J=7.5 Hz), 3.11 (1H, sep, J=7 Hz), 3.67 (3H, s), 7.11 (1H, s), 7.19 (2H, $A_2B_2$, J=8.5 Hz), 7.56 (2H, $A_2B_2$, J=8.5 Hz), 7.85 (1H, br s, NH)

The aforementioned methyl ester (90 mg, 0.252 mmol) was hydrolyzed in the same manner as that of Example 2, and the residue was recrystallized to obtain the title compound (6, 84 mg, 97%, 81% overall) as colorless prisms.

Mp: 139-141° C. ($CH_2Cl_2$-hexane)
MS (m/z): 343 ($M^+$, 24), 328 (5), 284 (4), 179 (100), 91 (10), 77 (10), 43 (11), 41 (9)
IR (KBr) $cm^{-1}$: 1724, 1635
$^1$H-NMR ($CDCl_3$) δ: 1.17 (6H, d, J=7 Hz), 1.31 (6H, d, J=7 Hz), 2.68 (2H, t, J=7.5 Hz), 2.83 (1H, sep, J=7 Hz), 2.95 (2H, t, J=7.5 Hz), 3.10 (1H, sep, J=7 Hz), 7.12 (1H, s), 7.20 (2H, $A_2B_2$, J=8.5 Hz), 7.56 (2H, $A_2B_2$, J=8.5 Hz), 7.88 (1H, br s, NH).

Example 8

5-[(4,5-Diisopropylfuran-2-carbonyl)amino]pyridine-2-carboxylic acid (7)

[Formula 9]

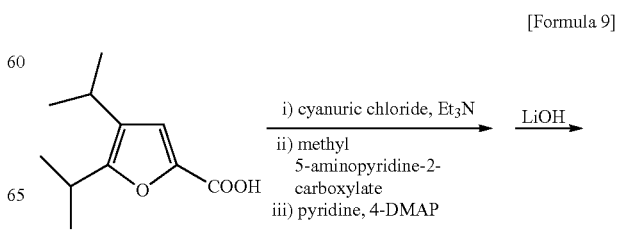

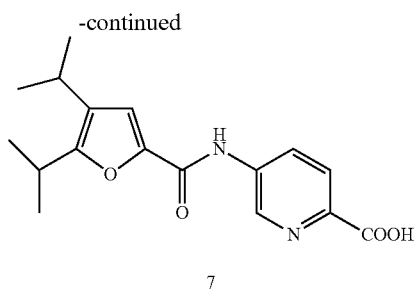

7

In the same manner as that of Example 2, 4,5-diisopropylfuran-2-carboxylic acid (86 mg, 0.439 mmol) was condensed with methyl 5-aminopyridine-2-carboxylate, and the resultant was purified by silica gel chromatography (3% methanol-chloroform) to obtain methyl 5-[(4,5-diisopropylfuran-2-carbonyl)amino]pyridine-2-carboxylate (111 mg, 77%) as colorless prisms.

Mp: 186.5-187.5° C. (CH$_2$Cl$_2$-hexane)

MS (m/z): 330 (M$^+$, 21), 179 (100), 108 (5), 93 (6), 91 (6), 77 (6), 65 (6)

IR (KBr) cm$^{-1}$: 1720, 1666

$^1$H-NMR (CDCl$_3$) δ: 1.19 (6H, d, J=7 Hz), 1.33 (6H, d, J=7 Hz), 2.86 (1H, sep, J=7 Hz), 3.14 (1H, sep, J=7 Hz), 4.01 (3H, s), 7.20 (1H, s), 8.07 (1H, br s, NH), 8.17 (1H, d, J=8.5 Hz), 8.52 (1H, dd, J=8.5, 3 Hz), 8.75 (11-1, d, J=3 Hz)

The aforementioned methyl ester (46 mg, 0.139 mmol) was hydrolyzed in the same manner as that of Example 2, and the residue was recrystallized to obtain the title compound (7, 42 mg, 95%, 73% overall) as colorless prisms.

Mp: 106-107.5° C. (CH$_2$Cl$_2$-hexane)

MS (m/z): 316 (M$^+$, 15), 179 (100), 121 (5), 108 (6), 93 (8), 91 (8), 77 (8), 65 (7), 43 (16), 41 (16)

IR (KBr) cm$^{-1}$: 1654

$^1$H-NMR (CDCl$_3$) δ: 1.19 (6H, d, J=7 Hz), 1.33 (6H, d, J=7 Hz), 2.86 (1H, sep, J=7 Hz), 3.15 (1H, sep, J=7 Hz), 7.23 (1H, s), 8.12 (1H, br s, NH), 8.23 (1H, d, J=8.5 Hz), 8.39 (1H, dd, J=8.5, 2.5 Hz), 8.88 (1H, d, J=2.5 Hz).

Example 9

6-[(4,5-Diisopropylfuran-2-carbonyl)amino]pyridine-3-carboxylic acid (8)

A solution of 4,5-diisopropylfuran-2-carboxylic acid (92 mg, 0.469 mmol) as the starting material in benzene (3 ml) was added with thionyl chloride (137 μl, 1.88 mmol) and dimethylformamide (1 drop), and the mixture was refluxed by heating for 1 hour with stirring. The solvent was evaporated under reduced pressure, then the residue was added with benzene (3 ml) again, and the mixture was evaporated to dryness. The residue was dissolved in pyridine (3 ml), the solution was added with methyl 2-aminopyridine-3-carboxylate (143 mg, 0.941 mmol) and 4-dimethylaminopyridine (2 mg, 16.4 μmol), and the mixture was stirred at room temperature for 24 hours. Pyridine was evaporated, then the residue was added with saturated aqueous ammonium chloride, and the mixture was extracted with ethyl acetate. The reaction mixture was treated in a conventional manner, and then the resultant was purified by silica gel chromatography (0.5% methanol-chloroform then 20% methanol-chloroform) to collect methyl 6-[(4,5-diisopropylfuran-2-carbonyl)amino]pyridine-3-carboxylate (100 mg, 65%) as colorless prisms as well as methyl 2-aminopyridine-3-carboxylate (63 mg) and the starting material (21 mg, 23%) in this order from the high polarity portion.

Mp: 89.5-90° C. (CH$_2$Cl$_2$-hexane)

MS (m/z): 330 (M$^+$, 49), 287 (55), 259 (42), 192 (100), 179 (58), 121 (36), 69 (61), 43 (49), 41 (61)

IR (KBr) cm$^{-1}$: 1730, 1713, 1672

$^1$H-NMR (CDCl$_3$) δ: 1.19 (6H, d, J=7 Hz), 1.31 (6H, d, J=7 Hz), 2.85 (1H, sep, J=7 Hz), 3.12 (1H, sep, J=7 Hz), 3.94 (3H, s), 7.22 (1H, s), 8.32 (1H, dd, J=8.5, 2.5 Hz), 8.43 (1H, d, J=8.5 Hz), 8.85 (1H, br s, NH), 8.94 (1H, d, J=2.5 Hz)

The aforementioned methyl ester (52 mg, 0.158 mmol) was hydrolyzed in the same manner as that of Example 2, and the residue was recrystallized to obtain the title compound (8, 45 mg, 90%, 59% overall) as colorless prisms.

Mp: 278-279° C. (MeOH—CH$_2$Cl$_2$)

MS (m/z): 316 (M$^+$, 45), 301 (11), 273 (60), 245 (42), 178 (100), 91 (24), 77 (24), 65 (22), 43 (55), 41 (39)

IR (KBr) cm$^{-1}$: 1684

$^1$H-NMR (DMSO-d$_6$) δ: 1.14 (6H, d, J=7 Hz), 1.25 (6H, d, J=7 Hz), 2.87 (1H, sep, J=7 Hz), 3.14 (1H, sep, J=7 Hz), 7.58 (1H, s), 8.25 (1H, dd, J=8.5, 1 Hz), 8.29 (1H, dd, J=8.5, 2.5 Hz), 8.87 (1H, dd, J=2.5, 1 Hz), 10.75 (1H, br s, NH), 13.17 (1H, br s, COOH).

Example 10

5-[(4,5-Diisopropylfuran-2-carbonyl)amino]thiophene-2-carboxylic acid (9)

[Formula 10]

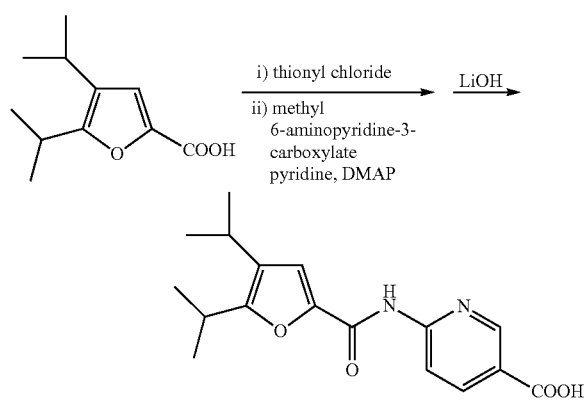

8

[Formula 11]

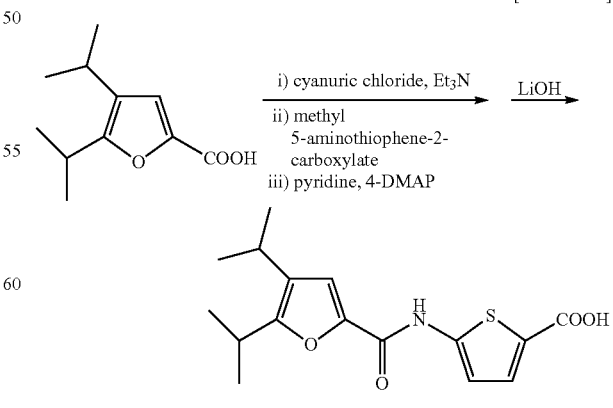

9

In the same manner as that of Example 2, 4,5-diisopropylfuran-2-carboxylic acid (42 mg, 0.214 mmol) was condensed with methyl 5-aminothiophene-2-carboxylate (50 mg, 0.318 mmol), and the resultant was purified by silica gel chromatography (2% methanol-chloroform) to obtain methyl 5-[(4,5-diisopropylfuran-2-carbonyl)amino]thiophene-2-carboxylate (39 mg, 54%) as pale yellow prisms.

Mp: 175-177° C. (CH$_2$Cl$_2$-hexane)

MS (m/z): 335 (M$^+$, 13), 179 (100), 108 (5), 96 (6), 43 (8), 41 (6)

IR (KBr) cm$^{-1}$: 1696, 1637

$^1$H-NMR (CDCl$_3$) δ: 1.18 (6H, d, J=7 Hz), 1.31 (6H, d, J=7 Hz), 2.84 (1H, sep, J=7 Hz), 3.12 (1H, sep, J=7 Hz), 3.78 (3H, s), 6.74 (1H, d, J=4 Hz), 7.20 (1H, s), 7.66 (1H, d, J=4 Hz), 8.65 (1H, br s, NH)

The aforementioned methyl ester (27 mg, 0.081 mmol) was hydrolyzed in the same manner as that of Example 2, and the residue was recrystallized to obtain the title compound (9, 24 mg, 93%, 50% overall) as colorless needles.

Mp: 227-228.5° C. (CH$_2$Cl$_2$)

MS (m/z): 321 (M$^+$, 10), 277 (3), 179 (100), 108 (5), 96 (7), 43 (9), 41 (9)

IR (KBr) cm$^{-1}$: 1657

$^1$H-NMR (CDCl$_3$) δ: 1.18 (6H, d, J=7 Hz), 1.32 (6H, d, J=7 Hz), 2.85 (1H, sep, J=7 Hz), 3.13 (1H, sep, J=7 Hz), 6.77 (1H, d, J=4 Hz), 7.22 (1H, s), 7.72 (1H, d, J=4 Hz), 8.67 (1H, br s, NH).

Example 11

4,5-Diisopropylfurfural

[Formula 12]

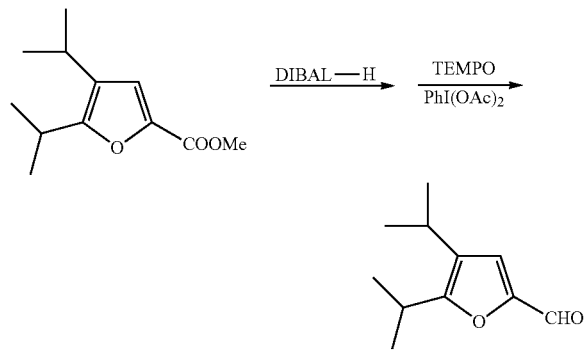

A solution of methyl 4,5-diisopropylfuran-2-carboxylate (1.44 g, 6.86 mmol) in dichloromethane (30 ml) was cooled to −78° C. under an argon atmosphere, and added dropwise with a solution of diisobutylaluminum hydride (0.93 M in hexane, 15.5 ml, 14.4 mmol) over 2 minutes. The reaction mixture was further stirred for 1 hour, and then poured into an aqueous ammonium chloride-ice bath, and the mixture was vigorously stirred. The reaction mixture was added with Celite, the mixture was filtered under reduced pressure, and the filtrate was extracted with chloroform. The reaction mixture was treated in a conventional manner, and then the resultant was purified by silica gel chromatography [hexane-ethyl acetate (9:1)] to obtain 4,5-diisopropylfuran-2-methyl alcohol (1.175 g, 94%) as colorless oil.

$^1$H-NMR (CDCl$_3$) δ: 1.13 (6H, d, J=7 Hz), 1.23 (6H, d, J=7 Hz), 1.74 (1H, br s, OH), 2.79 (1H, sep, J=7 Hz), 3.00 (1H, sep, J=7 Hz), 4.52 (2H, br s), 6.14 (1H, s)

A solution of the aforementioned alcohol (158 mg, 0.868 mmol) in dichloromethane (8 ml) was cooled on ice, and added with 2,2,6,6-tetramethylpiperidinoxy free radical (12 mg, 76.9 μmol) and iodobenzenediacetic acid (363 mg, 1.13 mmol), and the mixture was stirred for 15 minutes. The mixture was further stirred at room temperature for 3.5 hours, and then added with saturated aqueous sodium thiosulfate, and the mixture was extracted with ethyl acetate. The reaction mixture was treated in a conventional manner, and then the resultant was purified by silica gel chromatography [hexane-ethyl acetate (8:1)] to obtain the title compound (110 mg, 70%, 66% overall) as colorless oil.

$^1$H-NMR (CDCl$_3$) δ: 1.19 (6H, d, J=7 Hz), 1.30 (6H, d, J=7 Hz), 2.86 (1H, sep, J=7 Hz), 3.12 (1H, sep, J=7 Hz), 7.13 (1H, s), 9.49 (1H, s)

Example 12

Methyl 4-[(diethoxyphosphoryl)acetamino]benzoate

[Formula 13]

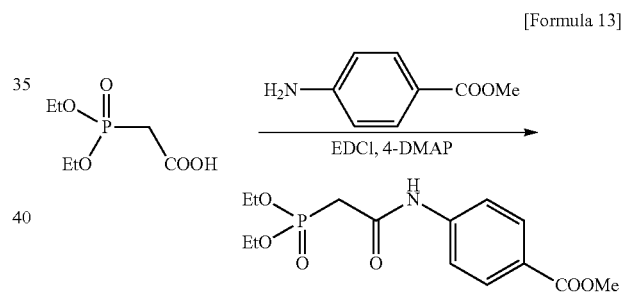

An ice-cooled solution of diethylphosphonoacetic acid (1.05 g, 5.36 mmol) in dichloromethane (10 ml) was added with 1-ethyl-3-(3-dimethylaminopropyl)carbodiimide hydrochloride (1.44 g, 7.50 mmol), methyl 4-aminobenzoate (0.89 g, 5.89 mmol) and 4-dimethylaminopyridine (33 mg, 0.270 mmol) in this order, and the mixture was stirred under an argon atmosphere for 30 minutes, and at room temperature for further 2 hours. The reaction mixture was added with aqueous ammonium chloride, and the mixture was extracted with chloroform. The reaction mixture was treated in a conventional manner, and then the resultant was purified by silica gel chromatography [benzene-ethyl acetate (1:1)] to obtain the title compound (1.655 g, 94%) as colorless prisms.

Mp: 72.5-73° C. (Et$_2$O-hexane)

MS (m/z): 329 (M$^+$, 28), 298 (5), 179 (9), 151 (100), 125 (39), 123 (18), 120 (35), 97 (22).

IR (KBr) cm$^{-1}$: 1715, 1694, 1682

$^1$H-NMR (CDCl$_3$) δ: 1.39 (6H, t, J=7 Hz), 3.11 (2H, d, J=21.5 Hz), 3.88 (3H, s), 4.21 (2H, q, J=7 Hz), 4.23 (2H, q, J=7 Hz), 7.53 (2H, A$_2$B$_2$, J=8.5 Hz), 7.83 (2H, A$_2$B$_2$, J=8.5 Hz), 9.70 (1H, br s, NH)

Example 13

4-[[3-(4,5-Diisopropyl-2-furanyl)acryloyl]amino]benzoic acid (10)

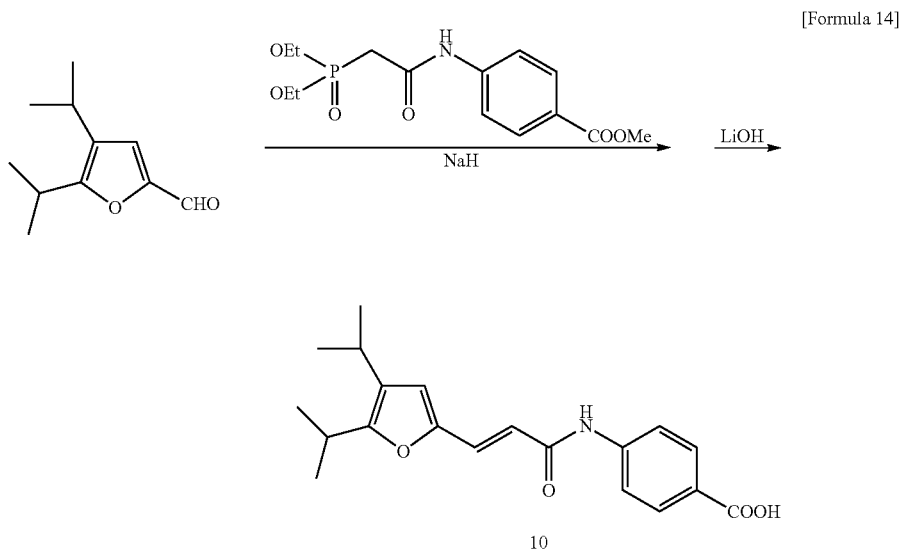

A solution of methyl 4-[(diethoxyphosphoryl)acetamino]benzoate (165 mg, 0.501 mmol) in anhydrous tetrahydrofuran (3 ml) was cooled on an ice bath, and added with sodium hydride (60% mineral oil dispersion, 20 mg, 0.50 mmol) under an argon atmosphere, and the mixture was stirred for 5 minutes. The reaction mixture was added dropwise with a solution of 4,5-diisopropylfurfural (60 mg, 0.33 mmol) in anhydrous tetrahydrofuran (2 ml), and the mixture was further stirred at 0° C. for 50 minutes. The reaction mixture was added with saturated aqueous ammonium chloride, and the mixture was extracted with chloroform. The reaction mixture was treated in a conventional manner, and then the resultant was purified by silica gel chromatography (2% methanol-chloroform) to obtain methyl 4-[[3-(4,5-diisopropyl-2-furanyl)acryloyl]amino]benzoate (115 mg, 97%) as colorless syrup-like substance.

MS (m/z): 355 (M$^+$, 13), 205 (100), 91 (14), 43 (20), 41 (10)

IR (CHCl$_3$) cm$^{-1}$: 1708, 1680, 1621

$^1$H-NMR (CDCl$_3$) δ: 1.15 (6H, d, J=7 Hz), 1.26 (6H, d, J=7 Hz), 2.80 (1H, sep, J=7 Hz), 3.05 (1H, sep, J=7 Hz), 3.90 (3H, s), 6.35 (1H, d, J=15 Hz), 6.48 (1H, s), 7.45 (1H, d, J=15 Hz), 7.66 (1H, br s, NH), 7.71 (2H, A$_2$B$_2$, J=8.5 Hz), 8.01 (2H, A$_2$B$_2$, J=8.5 Hz)

The methyl ester obtained above (11 mg, 0.313 mmol) was hydrolyzed in the same manner as that of Example 2, and the residue was recrystallized to obtain the title compound (10, 9.5 mg, 90%, 87% overall) as colorless needles.

Mp: 131-133° C. (CH$_2$Cl$_2$)

MS (m/z): 341 (M$^+$, 13), 205 (100), 147 (6), 91 (16), 65 (13), 43 (20), 41 (13)

IR (KBr) cm$^{-1}$: 1683, 1617, 1590

$^1$H-NMR (CDCl$_3$) δ: 1.16 (6H, d, J=7 Hz), 1.28 (6H, d, J=7 Hz), 2.81 (1H, sep, J=7 Hz), 3.07 (1H, sep, J=7 Hz), 6.23 (1H, d, J=15 Hz), 6.52 (1H, s), 7.46 (1H, d, J=15 Hz), 7.72 (2H, A$_2$B$_2$, J=8.5 Hz), 8.08 (2H, A$_2$B$_2$, J=8.5 Hz)

Example 14

2-Acetyl-4,5-diisopropylfuran

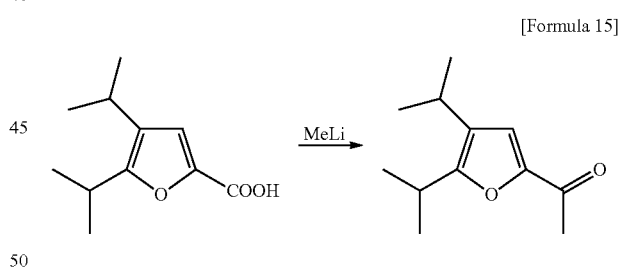

A solution of 4,5-diisopropylfuran-2-carboxylic acid (196 mg, 1.00 mmol) in diethyl ether (6 ml) was cooled to −18° C., and added dropwise with methyllithium (1.2 M in Et$_2$O, 2.5 ml, 3 mmol), and the mixture was stirred for 45 minutes. The reaction mixture was added with saturated aqueous ammonium chloride, and the mixture was extracted with diethyl ether. The reaction mixture was treated in a conventional manner, and then the resultant was purified by silica gel chromatography [hexane-ethyl acetate (7:1)] to obtain the title compound (162 mg, 84%) as colorless oil.

IR (neat) cm$^{-1}$: 1668

$^1$H-NMR (CDCl$_3$) δ: 1.17 (6H, d, J=7 Hz), 1.29 (6H, d, J=7 Hz), 2.42 (3H, s), 2.84 (1H, sep, J=7 Hz), 3.09 (1H, sep, J=7 Hz), 7.08 (1H, s)

Example 15

4-[[3-(4,5-Diisopropyl-2-furanyl)crotonoyl]amino]benzoic acid (11)

[Formula 16]

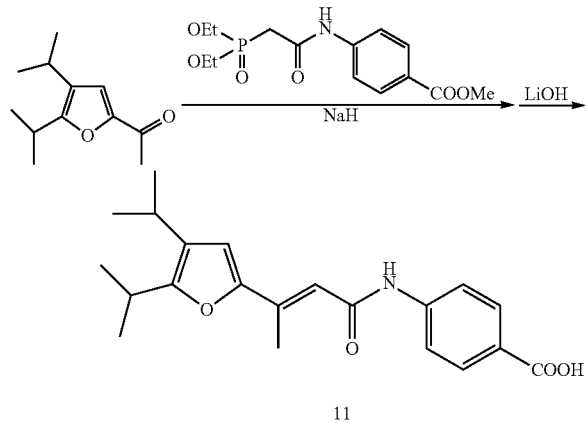

11

In the same manner as that of Example 13, a solution of methyl 4-[(diethoxyphosphoryl)acetamino]benzoate (271 mg, 0.823 mmol) in anhydrous tetrahydrofuran (4 ml) was cooled on an ice bath, and added with sodium hydride (60% mineral oil dispersion, 33 mg, 0.825 mmol) under an argon atmosphere, and the mixture was stirred for 10 minutes. The reaction mixture was added dropwise with a solution of 2-acetyl-4,5-diisopropylfuran (40 mg, 0.206 mmol) in anhydrous tetrahydrofuran (2 ml), the mixture was stirred at room temperature for 1 hour, and then further stirred under reflux by heating for 18 hours. The mixture was added with saturated aqueous ammonium chloride, and the mixture was extracted with ethyl acetate. The reaction mixture was treated in a conventional manner, and then the resultant was purified by silica gel chromatography [hexane-ethyl acetate (9:1)] to obtain, together with the collected starting material (15 mg, 38%), a crude product (40 mg) containing the title compound. The latter product was further purified by silica gel chromatography [benzene-ethyl acetate (49:1)] to obtain methyl 4-[[3-(4,5-diisopropyl-2-furanyl)crotonoyl]amino]benzoate (23 mg, 30%) as colorless needles.

Mp: 167-169° C. ($CH_2Cl_2$-hexane)

MS (m/z): 369 ($M^+$, 11), 354 (1), 338 (1), 310 (1), 219 (100), 120 (5), 109 (5), 105 (4), 91 (8), 43 (16). IR (KBr) $cm^{-1}$: 1715, 1653, 1614

$^1$H-NMR ($CDCl_3$) δ: 1.16 (6H, d, J=7 Hz), 1.26 (6H, d, J=7 Hz), 2.51 (3H, d, J=1 Hz), 2.81 (1H, sep, J=7 Hz), 3.04 (1H, sep, J=7 Hz), 3.90 (3H, s), 6.33-6.36 (1H, m), 6.34 (1H, s), 7.69 (2H, $A_2B_2$, J=8.5 Hz), 7.71 (1H, br s, NH), 8.00 (2H, $A_2B_2$, J=8.5 Hz)

The aforementioned methyl ester (35 mg, 94.9 μmol) was hydrolyzed in the same manner as that of Example 2, and the residue was recrystallized to obtain the title compound (11, 31 mg, 92%, 28% overall) as colorless needles.

Mp: 232.5-235° C. ($CH_2Cl_2$)

MS (m/z): 355 ($M^+$, 15), 340 (2), 219 (100), 109 (5), 91 (6), 65 (5), 43 (15)

IR (KBr) $cm^{-1}$: 1681, 1652 $^1$H-NMR ($CDCl_3$) δ: 1.17 (6H, d, J=7 Hz), 1.29 (6H, d, J=7 Hz), 2.51 (3H, d, J=0.5 Hz), 2.82 (1H, sep, J=7 Hz), 3.06 (1H, sep, J=7 Hz), 6.30 (1H, br s), 6.56 (1H, s), 7.43 (1H, br s), 7.71 (2H, $A_2B_2$, J=9 Hz), 8.08 (2H, $A_2B_2$, J=9 Hz).

Example 16

Polyisopropylpyrrole-2-carboxylic acid

[Formula 17]

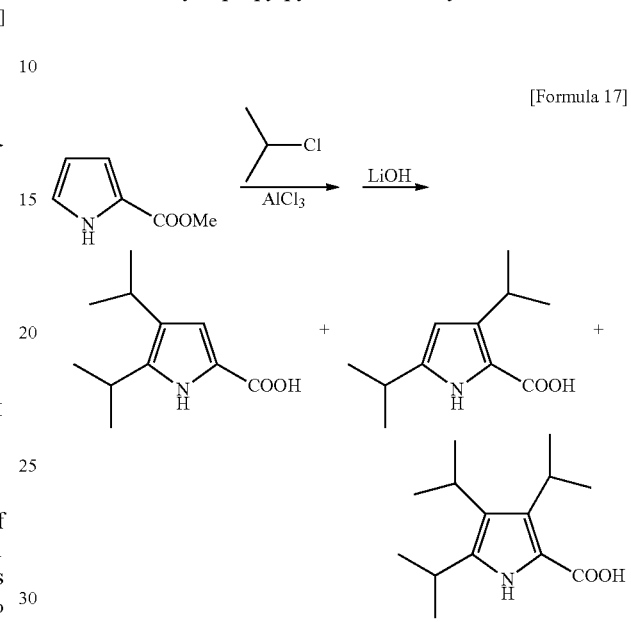

In the same manner as that of Example 1, methyl pyrrole-2-carboxylate (25.00 g, 0.200 mol) and 2-chloropropane (54.8 ml, 0.60 mol) were reacted (38 hours) in carbon disulfide (300 ml) in the presence of anhydrous aluminum chloride (59.9 g, 0.450 mol), and then the resultant was purified by silica gel chromatography [benzene-hexane (1:1)] to obtain methyl 3,4,5-triisopropylpyrrole-2-carboxylate (3.075 g, 6%), methyl 3,5-diisopropylpyrrole-2-carboxylate (7.448 g, 18%), and methyl 4,5-diisopropylpyrrole-2-carboxylate (1.733 g, 4%) in the order of polarity from the lowest.

Methyl 4,5-diisopropylpyrrole-2-carboxylate colorless prisms, Mp: 118-119° C. ($CH_2Cl_2$-hexane)
IR (KBr) $cm^{-1}$: 1667
$^1$H-NMR ($CDCl_3$) δ: 1.18 (6H, d, J=7 Hz), 1.26 (6H, d, J=7 Hz), 2.84 (1H, sep, J=7 Hz), 3.10 (1H, sep, J=7 Hz), 3.82 (3H, s), 6.77 (1H, d, J=3 Hz), 8.92 (1H, br s, NH)

Methyl 3,5-diisopropylpyrrole-2-carboxylate colorless scales, Mp: 56-58° C. (hexane)
IR (KBr) $cm^{-1}$: 1684, 1663
$^1$H-NMR ($CDCl_3$) δ: 1.20 (6H, d, J=7 Hz), 1.26 (6H, d, J=7 Hz), 2.90 (1H, sep, J=7 Hz), 3.49 (1H, sep, J=7 Hz), 3.83 (3H, s), 5.93 (1H, d, J=3 Hz), 8.57 (1H, br s, NH)

Methyl 3,4,5-triisopropylpyrrole-2-carboxylate colorless prisms, Mp: 155-156° C. ($CH_2Cl_2$.MeOH)
MS (m/z): 251 ($M^+$, 41), 236 (100), 204 (85), 91 (13), 77 (11), 41 (19). IR (KBr) $cm^{-1}$: 1662, 1651. $^1$H-NMR ($CDCl_3$) δ: 1.24 (6H, d, J=7 Hz), 1.26 (6H, d, J=7 Hz), 1.32 (6H, d, J=7 Hz), 3.07 (1H, sep, J=7 Hz), 3.16 (1H, sep, J=7 Hz), 3.52 (1H, br sep, J=7 Hz), 3.81 (3H, s), 8.49 (1H, br s, NH)

The three kinds of isomers obtained above (4,5-, 3,5- and 3,4,5-isomers) were each hydrolyzed in the same manner as that of Example 2, and the resultants were recrystallized to obtain 4,5-diisopropylpyrrole-2-carboxylic acid (164 mg from 195 mg, 90%, 3.6% overall), 3,5-diisopropylpyrrole-2-carboxylic acid (268 mg from 311 mg, 92%, 17% overall), and 3,4,5-triisopropylpyrrole-2-carboxylic acid (477 mg from 900 mg, 56%, 3.4% overall), respectively.

4,5-Diisopropylpyrrole-2-carboxylic acid colorless prisms, Mp: 94-95° C. ($CH_2Cl_2$-hexane)
MS (m/z): 195 ($M^+$, 34), 180 (100), 162 (90), 91 (13), 65 (13), 41 (17), 39 (16). IR (KBr) $cm^{-1}$: 1637. $^1$H-NMR ($CDCl_3$) δ: 1.19 (6H, d, J=6.5 Hz), 1.27 (6H, d, J=7 Hz), 2.85 (1H, sep, J=6.5 Hz), 3.11 (1H, sep, J=7 Hz), 6.92 (1H, d, J=2.5 Hz), 8.82 (1H, br s, NH), 11.80 (1H, br s, COOH)

3,5-Diisopropylpyrrole-2-carboxylic acid colorless prisms, Mp: 141-142° C. ($CH_2Cl_2$-hexane)
MS (m/z): 195 ($M^+$, 46), 180 (93), 162 (100), 41 (27), 39 (24)
IR (KBr) $cm^{-1}$: 1616
$^1$H-NMR ($CDCl_3$) δ: 1.22 (6H, d, J=7 Hz), 1.27 (6H, d, J=7 Hz), 2.91 (1H, sep, J=7 Hz), 3.55 (1H, sep, J=7 Hz), 5.97 (1H, d, J=3 Hz), 8.68 (1H, br s, NH), 11.91 (1H, br s, COOH)

3,4,5-Triisopropylpyrrole-2-carboxylic acid colorless needles, Mp: 148-149° C. ($CH_2Cl_2$-MeOH)
MS (m/z): 237 ($M^+$, 41), 222 (100), 204 (81), 178 (25), 43 (32), 41 (35)
IR (KBr) $cm^{-1}$: 1712
$^1$H-NMR (DMSO-$d_6$) δ: 1.18 (12H, d, J=7 Hz), 1.22 (6H, d, J=7 Hz), 3.04 (1H, sep, J=7 Hz), 3.07 (1H, sep, J=7 Hz), ca. 3.50-3.65 (1H, m), 10.50 (1H, br s, NH), 11.81 (1H, br s, COOH).

Example 17

4-[(4,5-Diisopropylpyrrole-2-carbonyl)amino]benzoic acid (12)

A solution of 4,5-diisopropylpyrrole-2-carboxylic acid (78 mg, 0.400 mmol) and methyl 4-aminobenzoate (181 mg, 1.20 mmol) in dichloromethane (5 ml) was added with 1-ethyl-3-(3-dimethylaminopropyl)carbodiimide hydrochloride (192 mg, 1.00 mmol) under an argon atmosphere, and the mixture was stirred at room temperature for 2 hours. The reaction mixture was treated in a conventional manner, and then the resultant was purified by silica gel chromatography (0.5% methanol-chloroform) to obtain the desired condensate (27 mg, 21%) from the low polarity portion, and the acid anhydride (30 mg, 40%), the starting material, from the high polarity portion.

Methyl 4-[(4,5-diisopropylpyrrole-2-carbonyl) amino]benzoate colorless prisms, Mp: 257-258° C. ($CH_2Cl_2$-hexane)
MS (m/z): 328 ($M^+$, 21), 313 (5), 178 (100), 162 (11), 120 (18)
IR (KBr) $cm^{-1}$: 1690, 1649
$^1$H-NMR ($CDCl_3$) δ: 1.21 (6H, d, J=7 Hz), 1.27 (6H, d, J=7 Hz), 2.89 (1H, sep, J=7 Hz), 3.11 (1H, sep, J=7 Hz), 3.90 (3H, s), 6.57 (1H, d, J=2.5 Hz), 7.56 (1H, br s, CONH), 7.67 (2H, $A_2B_2$, J=9 Hz), 8.03 (2H, $A_2B_2$, J=9 Hz), 8.89 (1H, br s, NH)
Starting Material Acid Anhydride:
colorless needles, Mp: 189-190° C. ($CH_2Cl_2$-hexane)
MS (m/z): 372 ($M^+$, 4), 195 (36), 180 (75), 178 (59), 162 (100), 134 (17), 41 (29), 39 (28)
IR (KBr) $cm^{-1}$: 1724, 1672
$^1$H-NMR ($CDCl_3$) δ: 1.20 (12H, d, J=7 Hz), 1.28 (12H, d, J=7 Hz), 2.86 (2H, sep, J=7 Hz), 3.12 (2H, sep, J=7 Hz), 6.92 (2H, d, J=2.5 Hz), 8.79 (2H, br s, NH)

A solution of the aforementioned acid anhydride (27 mg, 72.6 μmol) and methyl 4-aminobenzoate (16 mg, 0.106 mmol) in toluene (2.5 ml) was refluxed by heating for 3 hours. The reaction mixture was treated in a conventional manner, and then the resultant was purified by silica gel chromatography (1.5% then 10% methanol-chloroform) to additionally obtain the aforementioned methyl ester (21 mg, 92%, total 38% overall) and 4,5-diisopropylpyrrole-2-carboxylic acid (12 mg, 85%, 17% overall) in the order of polarity from the lowest. The aforementioned methyl ester (32 mg, 97.6 μmol) was hydrolyzed in the same manner as that of Example 2, and the residue was recrystallized to obtain the title compound (12, 29 mg, 95%, 36% overall) as colorless prisms.

[Formula 18]

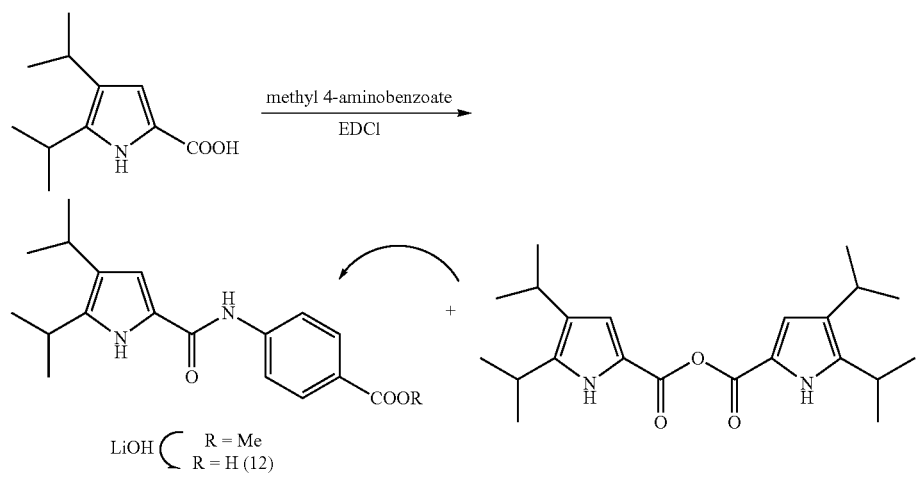

Mp: 230-230.5° C. (CH$_2$Cl$_2$-hexane)
MS (m/z): 314 (M$^+$, 21), 299 (5), 178 (100), 162 (9), 120 (16), 91 (7), 65 (8), 43 (13), 41 (9)
IR (KBr) cm$^{-1}$: 1697, 1645
$^1$H-NMR (DMSO-d$_6$) δ: 1.14 (6H, d, J=6.5 Hz), 1.22 (6H, d, J=7 Hz), 2.85 (1H, sep, J=6.5 Hz), 3.02 (1H, sep, J=7 Hz), 6.94 (1H, d, J=2.5 Hz), 7.84 (2H, A$_2$B$_2$, J=9 Hz), 7.88 (2H, A$_2$B$_2$, J=9 Hz), 9.79 (1H, s, CONH), 11.05 (1H, br s, NH), 12.58 (1H, br s, COOH)

Example 18

4-[(3,5-Diisopropylpyrrole-2-carbonyl)amino]benzoic acid (13)

[Formula 19]

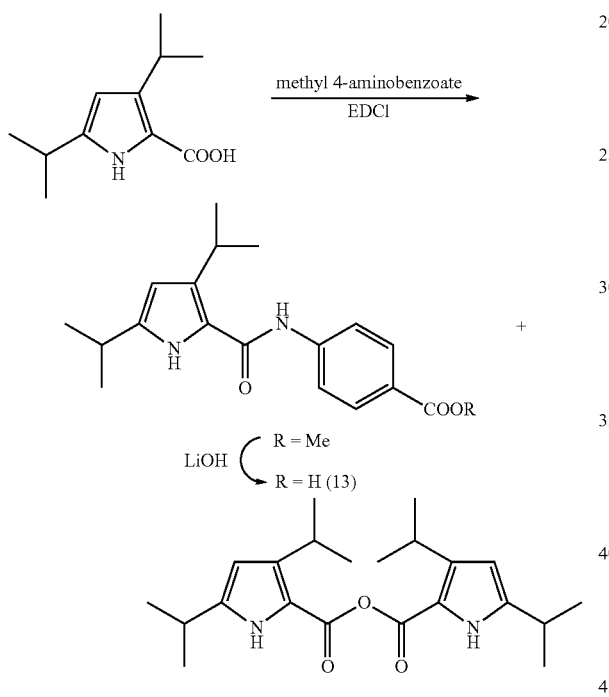

In the same manner as that of Example 17, 3,5-diisopropylpyrrole-2-carboxylic acid (60 mg, 0.308 mmol) was condensed with methyl 4-aminobenzoate, the reaction mixture was treated in a conventional manner, and then the resultant was purified by silica gel chromatography [hexane-ethyl acetate (3:1)] to obtain the desired condensate (60 mg, 59%) from the high polarity portion, and the starting material substrate acid anhydride (15 mg, 26%) from the low polarity portion.

Methyl 4-[(3,5-diisopropylpyrrole-2-carbonyl)amino]benzoate colorless prisms, Mp: 144-145.5° C. (CH$_2$Cl$_2$-hexane)
MS (m/z): 328 (M$^+$, 14), 178 (100), 120 (21)
IR (KBr) cm$^{-1}$: 1712, 1647
$^1$H-NMR (CDCl$_3$) δ: 1.27 (6H, d, J=7 Hz), 1.38 (6H, d, J=6.5 Hz), 2.92 (1H, sep, J=7 Hz), 3.18 (1H, sep, J=6.5 Hz), 3.91 (3H, s), 5.96 (1H, d, J=3 Hz), 7.61 (1H, br s, CONH), 7.65 (2H, A$_2$B$_2$, J=9 Hz), 8.03 (2H, A$_2$B$_2$, J=9 Hz), 9.01 (1H, br s, NH)

Starting Material Acid Anhydride:
colorless prisms, Mp: 200-201° C. (CH$_2$Cl$_2$-hexane)
MS (m/z): 372 (M$^+$, 2), 328 (1), 195 (22), 180 (41), 178 (100), 162 (44), 134 (14), 120 (13), 41 (12)
IR (KBr) cm$^{-1}$: 1708, 1669
$^1$H-NMR (CDCl$_3$) δ: 1.22 (12H, d, J=7 Hz), 1.27 (12H, d, J=7 Hz), 2.92 (2H, sep, J=7 Hz), 3.50 (2H, sep, J=7 Hz), 6.01 (2H, d, J=3 Hz), 8.78 (2H, br s, NH)

The aforementioned methyl ester (45 mg, 0.137 mmol) was hydrolyzed in the same manner as that of Example 2, and the residue was recrystallized to obtain the title compound (13, 41 mg, 95%, 56% overall) as colorless needles.
Mp: 225-226° C. (MeOH—CH$_2$Cl$_2$)
MS (m/z): 314 (M$^+$, 14), 178 (100), 120 (14), 65 (7), 45 (5), 43 (9), 41 (8)
IR (KBr) cm$^{-1}$: 1683, 1645
$^1$H-NMR (DMSO-d$_6$) δ: 1.13 (6H, d, J=7 Hz), 1.23 (6H, d, J=7 Hz), 2.89 (1H, sep, J=7 Hz), 3.59 (1H, sep, J=7 Hz), 5.90 (1H, d, J=2.5 Hz), 7.75 (2H, A$_2$B$_2$, J=9 Hz), 7.89 (2H, A$_2$B$_2$, J=9 Hz), 9.59 (1H, s, CONH), 10.90 (1H, br s, NH), 12.63 (1H, br s, COOH)

Example 19

4-[(3,4,5-Triisopropylpyrrole-2-carbonyl)amino]benzoic acid (14)

[Formula 20]

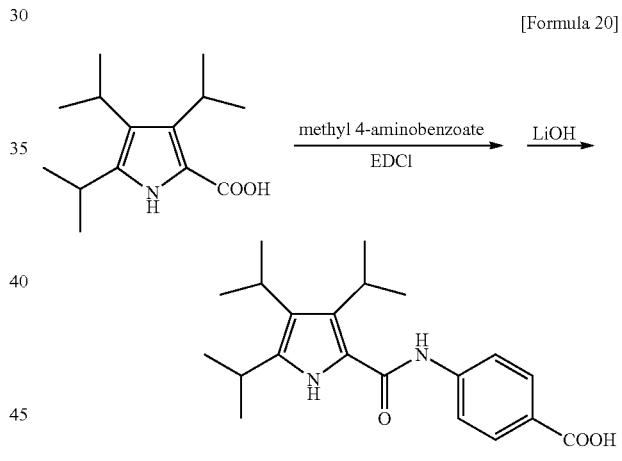

14

In the same manner as that of Example 17, 3,4,5-triisopropylpyrrole-2-carboxylic acid (50 mg, 0.211 mmol) was condensed with methyl 4-aminobenzoate, the reaction mixture was treated in a conventional manner, and then the resultant was recrystallized and purified by silica gel chromatography [hexane-ethyl acetate (14:1)] to obtain methyl 4-[(3,4,5-triisopropylpyrrole-2-carbonyl)amino]benzoate (59 mg, 76%) and the corrected starting material (5 mg, 10%).
Colorless prisms, Mp: 213-214° C. (CH$_2$Cl$_2$-hexane)
MS (m/z): 370 (M$^+$, 10), 220 (100), 204 (5), 120 (13)
IR (KBr) cm$^{-1}$: 1705, 1635
$^1$H-NMR (CDCl$_3$) δ: 1.24 (6H, d, J=7 Hz), 1.28 (6H, d, J=7 Hz), 1.45 (6H, d, J=7 Hz), 3.10 (1H, sep, J=7 Hz), 3.18 (1H, sep, J=7 Hz), 3.45 (1H, sep, J=7 Hz), 3.91 (3H, s), 7.61-7.65 (1H, br m, CONH), 7.64 (2H, A$_2$B$_2$, J=9 Hz), 8.02 (2H, A$_2$B$_2$, J=9 Hz), 8.77 (1H, br s, NH), The aforementioned methyl ester (43 mg, 0.206 mmol) was hydrolyzed in the same manner as that of Example 2, and the residue was recrystallized to obtain the title compound (14, 39 mg, 94%) as colorless prisms.

Mp: >300° C. (ethyl acetate-$CH_2Cl_2$)

MS (m/z): 356 ($M^+$, 13), 220 (100), 204 (6), 120 (10), 65 (6), 45 (6), 43 (9), 41 (8)

IR (KBr) $cm^{-1}$: 1684, 1631

$^1$H-NMR (DMSO-$d_6$) δ: 1.20 (6H, d, J=7 Hz), 1.23 (12H, d, J=7 Hz), 3.05 (1H, sep, J=7 Hz), 3.13 (1H, sep, J=7 Hz), 3.56 (1H, sep, J=7 Hz), 7.73 (2H, $A_2B_2$, J=8.5 Hz), 7.87 (2H, $A_2B_2$, J=8.5 Hz), 9.63 (1H, br s, CONH), 10.50 (1H, s, NH), 12.63 (1H, br s, COOH)

Example 20

4,5-Diisopropylthiophene-2-carboxylic acid

[Formula 21]

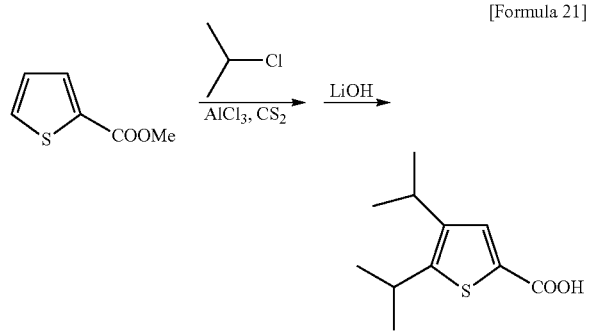

A suspension of anhydrous aluminum chloride (12.36 g, 92.9 mmol) in carbon disulfide (50 ml) was added with a solution of methyl thiophene-2-carboxylate (6.00 g, 42.3 mmol) in carbon disulfide (30 ml) and isopropyl chloride (1.20 ml, 13.1 mmol) at room temperature with stirring, and the mixture was stirred for 10 minutes. Then, the reaction mixture was slowly added dropwise with isopropyl chloride (8.50 ml, 93.0 mmol), and the mixture was further stirred at room temperature for 20 hours. The reaction mixture was poured into ice, and the mixture was extracted with ethyl acetate. The organic layer was washed with saturated aqueous sodium hydrogencarbonate, and treated in a conventional manner, and then the resultant was repeatedly purified by silica gel chromatography [hexane-ethyl acetate (99:1)] to obtain 3,5-diisopropyl isomer (54 mg, 0.6%), 4,5-diisopropyl isomer (5.12 g, 54%), and 5-monoisopropyl isomer (1.04 g, 13%) in the order of polarity from the lowest.

Methyl 3,5-diisopropylthiophene-2-carboxylate colorless oil

IR (neat) $cm^{-1}$: 1707

$^1$H-NMR (CDCl$_3$) δ: 1.22 (6H, d, J=7 Hz), 1.33 (6H, d, J=7 Hz), 3.13 (1H, sep, J=7 Hz), 3.83 (3H, s), 3.92 (1H, sep, J=7 Hz), 6.79 (1H, s)

Methyl 4,5-diisopropylthiophene-2-carboxylate colorless oil

IR (neat) $cm^{-1}$: 1709

$^1$H-NMR (CDCl$_3$) δ: 1.21 (6H, d, J=7 Hz), 1.31 (6H, d, J=7 Hz), 3.01 (1H, sep, J=7 Hz), 3.31 (1H, sep, J=7 Hz), 3.85 (3H, s), 7.62 (1H, s)

Methyl 5-isopropylthiophene-2-carboxylate colorless oil

IR (neat) $cm^{-1}$: 1708

$^1$H-NMR (CDCl$_3$) δ: 1.34 (6H, d, J=7 Hz), 3.18 (1H, sep, J=7 Hz), 3.85 (3H, s), 6.81 (1H, d, J=3.5 Hz), 7.63 (1H, d, J=3.5 Hz)

The aforementioned main product, 4,5-diisopropyl isomer (3.006 g, 13.3 mmol), was hydrolyzed in the same manner as that of Example 2, and the residue was recrystallized to obtain 4,5-diisopropylthiophene-2-carboxylic acid (2.531 g, 90%, 49% overall) as colorless prisms.

Mp: 149-151° C. ($CH_2Cl_2$-hexane)

MS (m/z): 212 ($M^+$, 29), 197 (100), 155 (18), 69 (22), 41 (28)

IR (KBr) $cm^{-1}$: 1656

$^1$H-NMR (CDCl$_3$) δ: 1.22 (6H, d, J=7 Hz), 1.33 (6H, d, J=7 Hz), 3.03 (1H, sep, J=7 Hz), 3.33 (1H, sep, J=7 Hz), 7.70 (1H, s), ca. 10.00 (1H, br s, COOH).

Example 21

4-[(4,5-Diisopropylthiophene-2-carbonyl)amino]benzoic acid (15)

[Formula 22]

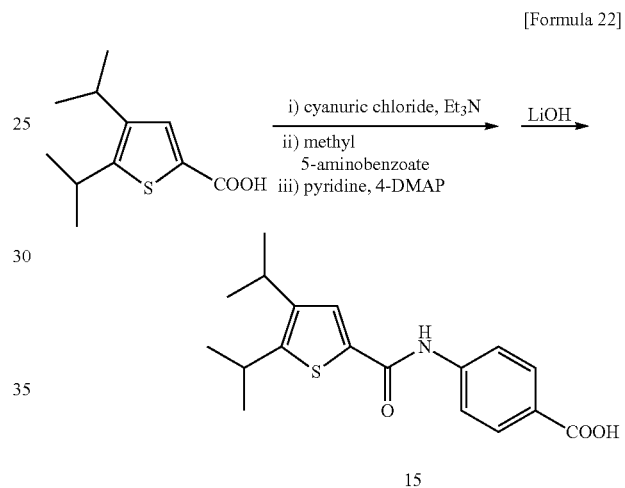

In the same manner as that of Example 2, 4,5-diisopropylthiophene-2-carboxylic acid (86 mg, 0.406 mmol) was condensed with methyl 4-aminobenzoate (123 mg, 0.815 mmol), and the resultant was purified by silica gel chromatography [hexane-ethyl acetate (3:1)] to obtain methyl 4-[(4,5-diisopropylthiophene-2-carbonyl)amino]benzoate (121 mg, 86%) as colorless needles.

Mp: 180-182.5° C. ($CH_2Cl_2$-hexane)

MS (m/z): 345 ($M^+$, 10), 195 (100), 152 (5), 137 (4), 119 (5), 91 (7)

IR (KBr) $cm^{-1}$: 1714, 1646, 1633

$^1$H-NMR (CDCl$_3$) δ: 1.24 (6H, d, J=7 Hz), 1.34 (6H, d, J=7 Hz), 3.09 (1H, sep, J=7 Hz), 3.34 (1H, sep, J=7 Hz), 3.91 (3H, s), 7.49 (1H, s), ca. 7.67-770 (1H, br, NH), 7.70 (2H, $A_2B_2$, J=8.5 Hz), 8.04 (2H, $A_2B_2$, J=8.5 Hz)

The aforementioned methyl ester (70 mg, 0.203 mmol) was hydrolyzed in the same manner as that of Example 2, and the residue was recrystallized to obtain the title compound (15, 64 mg, 95%, 82% overall) as colorless needles.

Mp: 219-221° C. (EtOAc-hexane)

MS (m/z): 331 ($M^+$, 10), 195 (100), 152 (5), 137 (5), 119 (5), 91 (7), 65 (6), 41 (7)

IR (KBr) $cm^{-1}$: 1683, 1646

$^1$H-NMR (DMSO-$d_6$) δ: 1.22 (6H, d, J=7 Hz), 1.27 (6H, d, J=7 Hz), 3.06 (1H, sep, J=7 Hz), ca. 3.32-3.45 (1H, m), 7.85 (2H, $A_2B_2$, J=8.5 Hz), 7.93 (2H, $A_2B_2$, J=8.5 Hz), 7.94 (1H, s), 10.29 (1H, s, NH), 12.75 (1H, br s, COOH)

Example 22

5-[(4,5-Diisopropylthiophene-2-carbonyl)amino]pyridine-2-carboxylic acid (16)

[Formula 23]

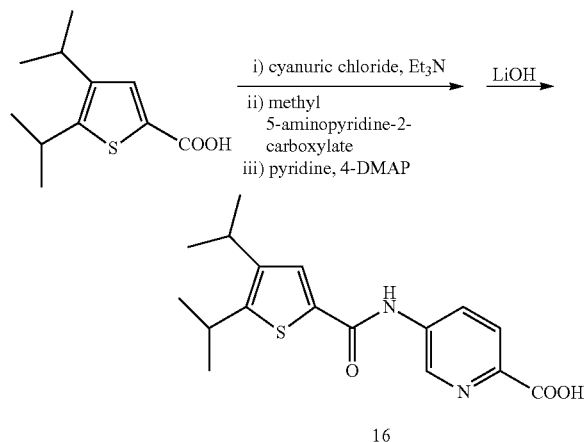

In the same manner as that of Example 2, 4,5-diisopropylthiophene-2-carboxylic acid (102 mg, 0.481 mmol) was condensed with methyl 5-aminopyridine-2-carboxylate, and the resultant was purified by silica gel chromatography [benzene-ethyl acetate (2:1)] to obtain methyl 5-[(4,5-diisopropylthiophene-2-carbonyl)amino]pyridine-2-carboxylate (112 mg, 67%) as colorless needles.

Mp: 207-208.5° C. ($CH_2Cl_2$-hexane)
MS (m/z): 346 ($M^+$, 7), 315 (1), 222 (2), 195 (100), 152 (6), 119 (5)
IR (KBr) $cm^{-1}$: 1717, 1662
$^1$H-NMR ($CDCl_3$) δ: 1.25 (6H, d, J=7 Hz), 1.34 (6H, d, J=7 Hz), 3.06 (1H, sep, J=7 Hz), 3.35 (1H, sep, J=7 Hz), 4.01 (3H, s), 7.54 (1H, s), 7.79 (1H, br s, NH), 8.17 (1H, d, J=8.5 Hz), 8.51 (1H, dd, J=8.5, 2.5 Hz), 8.71 (1H, d, J=2.5 Hz)

The aforementioned methyl ester (94 mg, 0.272 mmol) was hydrolyzed in the same manner as that of Example 2, and the residue was recrystallized to obtain the title compound (16, 83 mg, 92%, 62% overall) as colorless prisms.

Mp: 216-217° C. ($CH_2Cl_2$-benzene)
MS (m/z): 332 ($M^+$, 6), 195 (100), 152 (5), 137 (4), 119 (4), 91 (5), 45 (4), 43 (4), 41 (6)
IR (KBr) $cm^{-1}$: 1708, 1663, 1646
$^1$H-NMR (DMSO-$d_6$) δ: 1.22 (6H, d, J=7 Hz), 1.26 (6H, d, J=7 Hz), 3.06 (1H, sep, J=7 Hz), 3.35 (1H, sep, J=7 Hz), 7.94 (1H, s), 8.06 (1H, d, J=8.5 Hz), 8.33 (1H, dd, J=8.5, 2.5 Hz), 8.97 (1H, d, J=2.5 Hz), 10.50 (1H, br s, NH)

Example 23

6-[(4,5-Diisopropylthiophene-2-carbonyl)amino]pyridine-3-carboxylic acid (17)

[Formula 24]

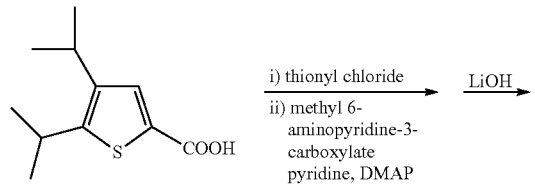

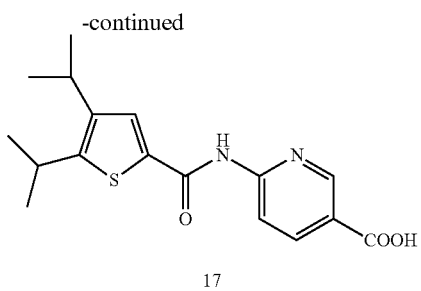

In the same manner as that of Example 9, 4,5-diisopropylthiophene-2-carboxylic acid (180 mg, 0.849 mmol) was converted to an acid chloride with thionyl chloride and dimethylformamide. This acid chloride was dissolved in pyridine (4 ml), the solution was added with methyl 2-aminopyridine-3-carboxylate (258 mg, 1.70 mmol) and 4-dimethylaminopyridine (5 mg, 41 μmol), and the mixture was stirred at room temperature for 48 hours. The reaction mixture was treated in a conventional manner, and then the resultant was purified by silica gel chromatography [benzene-ethyl acetate (4:1)] to obtain methyl 6-[(4,5-diisopropylthiophene-2-carbonyl)amino]pyridine-3-carboxylate (98 mg, 33%) as colorless foam, together with the collected starting material (67 mg, 37%).

MS (m/z): 346 ($M^+$, 15), 331 (2), 313 (17), 303 (4), 301 (4), 195 (100), 152 (6), 137 (5), 119 (5), 91 (7), 65 (6), 41 (7)
IR ($CHCl_3$) $cm^{-1}$: 1717, 1667
$^1$H-NMR ($CDCl_3$) δ: 1.20 (6H, d, J=7 Hz), 1.33 (6H, d, J=7 Hz), 3.04 (1H, sep, J=7 Hz), 3.33 (1H, sep, J=7 Hz), 3.93 (3H, s), 7.56 (1H, s), 8.32 (1H, dd, J=8.5, 2 Hz), 8.41 (1H, d, J=8.5 Hz), 8.89 (1H, br s), 8.96 (1H, br s, NH)

The aforementioned methyl ester (94 mg, 0.272 mmol) was hydrolyzed in the same manner as that of Example 2, and the residue was recrystallized to obtain the title compound (17, 67 mg, 74%, 24% overall) as colorless prisms.

Mp: >300° C. (MeOH—$CH_2Cl_2$)
MS (m/z): 332 ($M^+$, 14), 299 (14), 195 (100), 152 (5), 137 (5), 119 (5), 91 (7), 41 (7)
IR (KBr) $cm^{-1}$: 1677, 1604
$^1$H-NMR (DMSO-d6) δ: 1.19 (6H, d, J=7 Hz), 1.25 (6H, d, J=7 Hz), 3.03 (1H, sep, J=7 Hz), ca. 3.28-3.43 (1H, m, overlapping with DMSO), 8.23 (1H, s), 8.23 (1H, d, J=8.5 Hz), 8.28 (1H, dd, J=8.5, 2 Hz), 8.87 (1H, d, J=2 Hz), 11.09 (1H, br s, NH)

Example 24

2-Fluoro-4-[(4,5-diisopropylfuran-2-carbonyl)amino]benzoic acid (22)

[Formula 25]

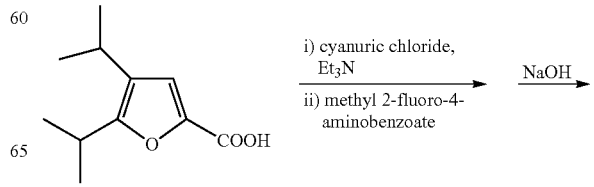

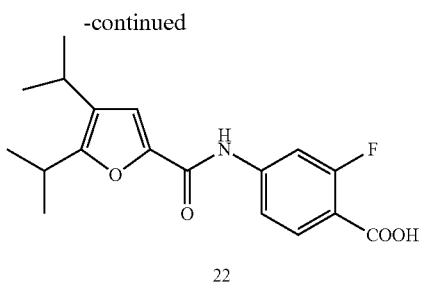

22

In the same manner as that of Example 2, 4,5-diisopropylfuran-2-carboxylic acid (80 mg, 0.408 mmol) and methyl 2-fluoro-4-aminobenzoate (125 mg, 0.739 mmol) were condensed, the reaction mixture was treated in a conventional manner, and then the residue was purified by silica gel chromatography [hexane-ethyl acetate (40:1)] and recrystallized to obtain methyl 2-fluoro-4-[(4,5-diisopropylfuran-2-carbonyl)amino]benzoate (95 mg, 67%) as colorless prisms.

Mp: 182-183° C. (CHCl$_3$-hexane)

$^1$H-NMR (CDCl$_3$) δ: 1.18 (6H, d, J=7 Hz), 1.31 (6H, d, J=7 Hz), 2.84 (1H, sep, J=7 Hz), 3.12 (1H, sep, J=7 Hz), 3.92 (3H, s), 7.18 (1H, s), 7.32 (1H, dd, J=9, 2 Hz), 7.75 (1H, dd, J=13, 2 Hz), 7.95 (1H, t, J=9 Hz), 8.04 (1H, br s, NH)

A solution of the aforementioned ester (92 mg, 0.265 mmol) in ethanol (5 ml) was added with 2 M aqueous sodium hydroxide (1 ml) to perform hydrolysis at room temperature for 4 hours, and extraction and recrystallization were performed to obtain the title compound (22, 77 mg, 86%) as colorless needles.

Mp: 151-152° C. (EtOAc-hexane)

$^1$H-NMR (CDCl$_3$) δ: 1.18 (6H, d, J=7 Hz), 1.32 (6H, d, J=7 Hz), 2.85 (1H, sep, J=7 Hz), 3.13 (1H, sep, J=7 Hz), 7.19 (1H, s), 7.35 (1H, dd, J=8, 2 Hz), 7.80 (1H, dd, J=13, 2 Hz), 8.02 (1H, t, J=8 Hz), 8.07 (1H, br s, NH)

Example 25

2-Chloro-4-[(4,5-diisopropylfuran-2-carbonyl)amino]benzoic acid (23)

[Formula 26]

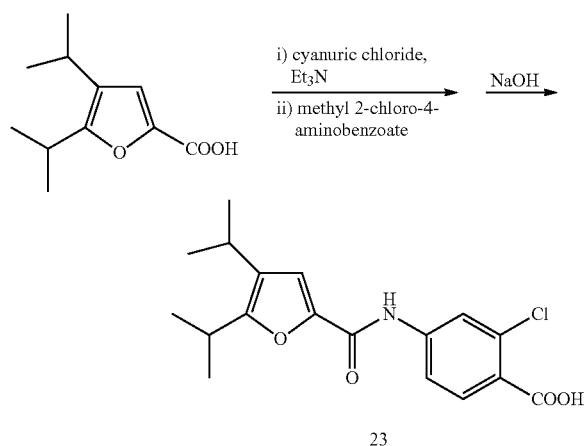

23

In the same manner as that of Example 24, 4,5-diisopropylfuran-2-carboxylic acid (80 mg, 0.408 mmol) and methyl 2-chloro-4-aminobenzoate (136 mg, 0.733 mmol) were condensed, the reaction mixture was treated in a conventional manner, and then the residue was purified by silica gel chromatography [hexane-ethyl acetate (40:1)] and recrystallized to obtain methyl 2-chloro-4-[(4,5-diisopropylfuran-2-carbonyl)amino]benzoate (106 mg, 72%) as colorless prisms.

Mp: 123-124° C. (CHCl$_3$-hexane)

$^1$H-NMR (CDCl$_3$) δ: 1.18 (6H, d, J=7 Hz), 1.31 (6H, d, J=7 Hz), 2.84 (1H, sep, J=7 Hz), 3.12 (1H, sep, J=7 Hz), 3.92 (3H, s), 7.17 (1H, s), 7.66 (1H, dd, J=9, 2 Hz), 7.82 (1H, d, J=2 Hz), 7391 (1H, d, J=9 Hz), 8.00 (1H, br s, NH)

The aforementioned ester (102 mg, 0.280 mmol) was hydrolyzed with sodium hydroxide in a conventional manner, and extraction and recrystallization were performed to obtain the title compound (23, 88 mg, 90%) as pale yellow needles.

Mp: 152-153° C. (EtOAc-hexane)

$^1$H-NMR (CDCl$_3$) δ: 1.18 (6H, d, J=7 Hz), 1.32 (6H, d, J=7 Hz), 2.85 (1H, sep, J=7 Hz), 3.13 (1H, sep, J=7 Hz), 7.19 (1H, s), 7.69 (1H, dd, J=9, 2 Hz), 7.88 (1H, d, J=2 Hz), 8.02 (1H, d, J=2 Hz), 8.08 (1H, br s, NH).

Example 26

2-Hydroxy-4-[(4,5-diisopropylfuran-2-carbonyl)amino]benzoic acid (24)

[Formula 27]

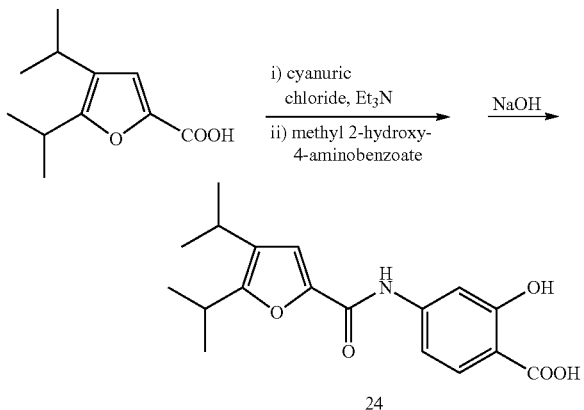

24

In the same manner as that of Example 24, 4,5-diisopropylfuran-2-carboxylic acid (80 mg, 0.408 mmol) and methyl 2-hydroxy-4-aminobenzoate (123 mg, 0.736 mmol) were condensed, the reaction mixture was treated in a conventional manner, and then the residue was purified by silica gel chromatography [hexane-ethyl acetate (50:1)] and recrystallized to obtain methyl 2-hydroxy-4-[(4,5-diisopropylfuran-2-carbonyl)amino]benzoate (101 mg, 72%) as colorless prisms.

Mp: 156-157° C. (CHCl$_3$-hexane)

$^1$H-NMR (CDCl$_3$) δ: 1.17 (6H, d, J=7 Hz), 1.31 (6H, d, J=7 Hz), 2.84 (1H, sep, J=7 Hz), 3.11 (1H, sep, J=7 Hz), 3.94 (3H, s), 7.16 (1H, s), 7.23 (1H, dd, J=9, 2 Hz), 7.31 (1H, d, J=2 Hz), 7.81 (1H, d, J=9 Hz), 7.98 (1H, br s, NH), 10.87 (1H, s, OH)

The aforementioned ester (95 mg, 0.275 mmol) was hydrolyzed with sodium hydroxide in a conventional manner, and extraction and recrystallization were performed to obtain the title compound (24, 71 mg, 78%) as colorless needles.

Mp: 179-180° C. (EtOAc-hexane)

$^1$H-NMR (CDCl$_3$) δ: 1.18 (6H, d, J=7 Hz), 1.32 (6H, d, J=7 Hz), 2.84 (1H, sep, J=7 Hz), 3.12 (1H, sep, J=7 Hz), 7.19 (1H, s), 7.24 (1H, dd, J=9, 2 Hz), 7.38 (1H, d, J=2 Hz), 7.89 (1H, d, J=9 Hz), 8.00 (1H, br s, NH), 10.59 (1H, s, OH)

Example 27

2-Methoxy-4-[(4,5-diisopropylfuran-2-carbonyl)amino]benzoic acid (25)

[Formula 28]

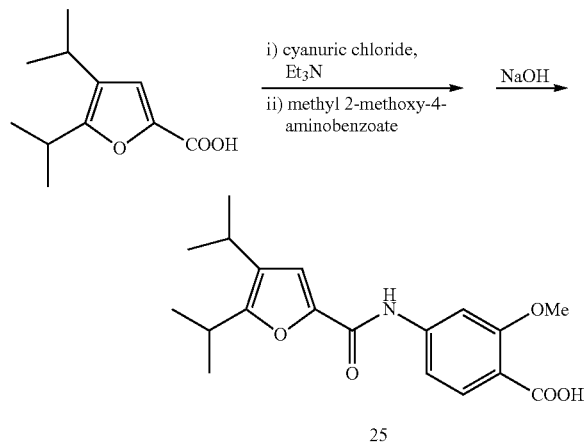

In the same manner as that of Example 24, 4,5-diisopropylfuran-2-carboxylic acid (80 mg, 0.408 mmol) and methyl 2-methoxy-4-aminobenzoate (133 mg, 0.734 mmol) were condensed, the reaction mixture was treated in a conventional manner, and then the residue was purified by silica gel chromatography [hexane-ethyl acetate (5:1)] to obtain methyl 2-methoxy-4-[(4,5-diisopropylfuran-2-carbonyl)amino]benzoate (65 mg, 45%).

$^1$H-NMR (CDCl$_3$) δ: 1.18 (6H, d, J=7 Hz), 1.32 (6H, d, J=7 Hz), 2.84 (1H, sep, J=7 Hz), 3.12 (1H, sep, J=7 Hz), 3.88 (3H, s), 3.96 (3H, s), 6.95 (1H, dd, J=8, 2 Hz), 7.15 (1H, s), 7.80 (1H, d, J=2 Hz), 7.85 (1H, d, J=8 Hz), 8.02 (1H, br s, NH)

The aforementioned ester (65 mg, 0.181 mmol) was hydrolyzed with sodium hydroxide in a conventional manner, and extraction and recrystallization were performed to obtain the title compound (25, 55 mg, 87%) as colorless needles.

Mp: 136-137° C. (CH$_2$Cl$_2$-hexane)

$^1$H-NMR (CDCl$_3$) δ: 1.19 (6H, d, J=7 Hz), 1.32 (6H, d, J=7 Hz), 2.85 (1H, sep, J=7 Hz), 3.13 (1H, sep, J=7 Hz), 4.13 (3H, s), 6.92 (1H, dd, J=9, 2 Hz), 7.17 (1H, s), 8.08 (1H, br s, NH), 8.13-8.16 (2H, m).

Example 28

2-Methoxy-4-[(4,5-diisopropylfuran-2-carbonyl)amino]benzoic acid (26)

[Formula 29]

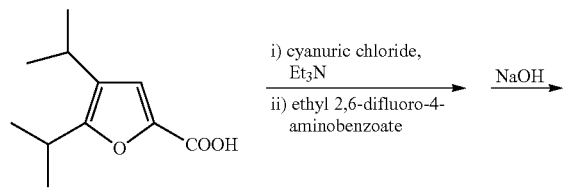

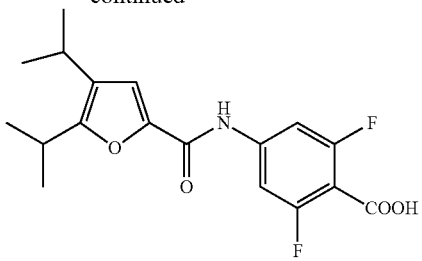

In the same manner as that of Example 24, 4,5-diisopropylfuran-2-carboxylic acid (80 mg, 0.408 mmol) and ethyl 2,6-difluoro-4-aminobenzoate (148 mg, 0.736 mmol) were condensed, the reaction mixture was treated in a conventional manner, and then the residue was purified by silica gel chromatography [n-hexane-ethyl acetate (40:1)] to obtain ethyl 2,6-difluoro-4-[(4,5-diisopropylfuran-2-carbonyl)amino]benzoate (105 mg, 68%).

$^1$H-NMR (CDCl$_3$) δ: 1.17 (6H, d, J=7 Hz), 1.31 (6H, d, J=7 Hz), 1.39 (3H, t, J=7 Hz), 2.84 (1H, sep, J=7 Hz), 3.12 (1H, sep, J=7 Hz), 4.40 (2H, q, J=7 Hz), 7.18 (1H, s), 7.37 (2H, d, J=10 Hz), 8.05 (1H, br s, NH)

The aforementioned ester (105 mg, 0.277 mmol) was hydrolyzed with sodium hydroxide in a conventional manner, and extraction and recrystallization were performed to obtain the title compound (26, 80 mg, 82%) as colorless needles.

Mp: 161-163° C. (EtOAc-hexane)

$^1$H-NMR (CDCl$_3$) δ: 1.18 (6H, d, J=7 Hz), 1.32 (6H, d, J=7 Hz), 2.85 (1H, sep, J=7 Hz), 3.13 (1H, sep, J=7 Hz), 7.21 (1H, s), 7.40 (2H, d, J=10 Hz), 8.03 (1H, br s, NH)

Example 29

4-[[3-(4,5-Diisopropyl-2-furanyl)acryloyl]methylamino]benzoic acid (27)

[Formula 30]

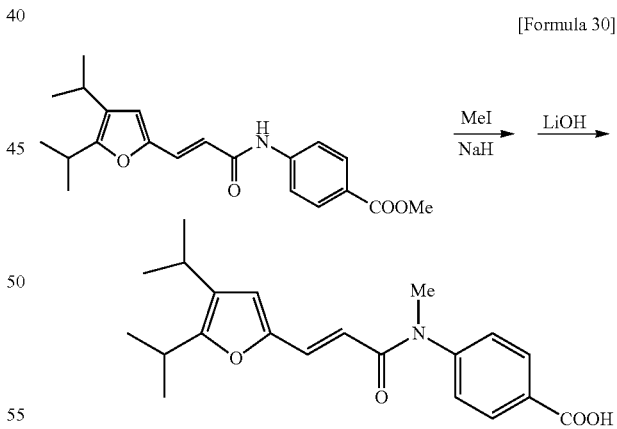

A solution of methyl 4-[[3-(4,5-diisopropyl-2-furanyl)acryloyl]amino]benzoate (93 mg, 0.262 mmol) in anhydrous THF (4 ml) was cooled on ice, and added successively with methyl iodide (33 μl, 1.06 mmol) and sodium hydride (60%, 21 mg, 0.525 mmol) under an argon atmosphere. The mixture was stirred for 3 hours, and then added with saturated aqueous ammonium chloride, and the mixture was extracted with ethyl acetate. The reaction mixture was treated in a conventional manner, and the resultant was purified by silica gel chromatography [benzene-ethyl acetate (14:1)] and recrystallized to obtain methyl 4-[[3-(4,5-diisopropyl-2-furanyl)acryloyl]methylamino]benzoate (87 mg, 90%) as colorless prisms.

Mp: 142-142.5° C. (CH$_2$Cl$_2$-hexane)

MS (m/z): 369 (M$^+$, 8), 338 (1), 310 (1), 205 (100), 91 (10), 59 (9), 43 (15), 41 (8),

IR (KBr) cm$^{-1}$: 1720, 1648

$^1$H-NMR (CDCl$_3$) δ: 1.12 (6H, d, J=7 Hz), 1.15 (6H, d, J=7 Hz), 2.76 (1H, sep, J=7 Hz), 2.97 (1H, sep, J=7 Hz), 3.42 (3H, s), 3.95 (3H, s), 6.17 (1H, d, J=15 Hz), 6.39 (1H, s), 7.35 (2H, A$_2$B$_2$, J=8.5 Hz), 7.42 (1H, dd, J=15 Hz), 8.17 (2H, A$_2$B$_2$, J=8.5 Hz)

The ester obtained above (68 mg, 0.314 μmol) was hydrolyzed with lithium hydroxide in a conventional manner, and the residue was recrystallized to obtain the title compound (27, 63 mg, 96%) as colorless prisms.

Mp: 213-214° C. (CH$_2$Cl$_2$-hexane)

MS (m/z): 355 (M$^+$, 10), 205 (100), 91 (11), 77 (9), 65 (11), 43 (22), 41 (13)

IR (KBr) cm$^{-1}$: 1706, 1639

$^1$H-NMR (CDCl$_3$) δ: 1.12 (6H, d, J=7 Hz), 1.15 (6H, d, J=7 Hz), 2.76 (1H, sep, J=7 Hz), 2.96 (1H, sep, J=7 Hz), 3.45 (3H, s), 6.17 (1H, d, J=15 Hz), 6.41 (1H, s), 7.35 (2H, A$_2$B$_2$, J=8.5 Hz), 7.41 (1H, dd, J=15 Hz), 8.16 (2H, A$_2$B$_2$, J=8.5 Hz)

Example 30

3-[[3-(4,5-Diisopropyl-2-furanyl)acryloyl]amino]benzoic acid (28)

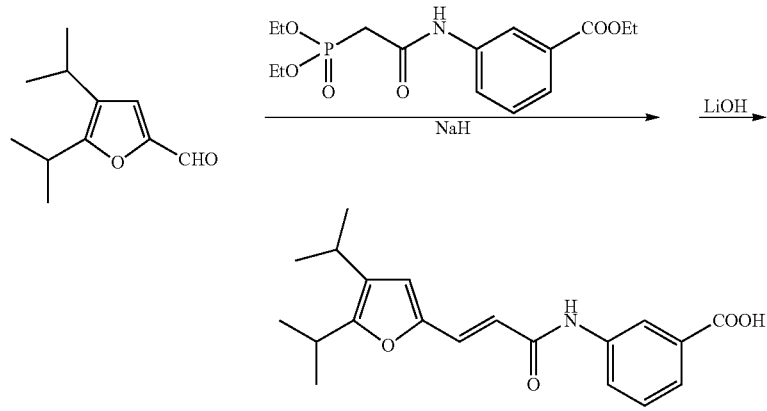

In the same manner as that of Example 13, ethyl 3-[(diethoxyphosphoryl)acetamino]benzoate (586 mg, 1.71 mmol) was allowed to act on 4,5-diisopropylfurfural (205 mg, 1.14 mmol), the reaction mixture was treated in a conventional manner, and then the resultant was purified by silica gel chromatography [benzene-ethyl acetate (19:1)] and recrystallized to obtain ethyl 3-[[3-(4,5-diisopropyl-2-furanyl)acryloyl]amino]benzoate (381 mg, 91%) as colorless fine needles.

Mp: 160-161° C. (CH$_2$Cl$_2$-hexane)

MS (m/z): 369 (M$^+$, 12), 324 (2), 205 (100), 203 (6), 91 (11), 55 (6), 43 (15), 41 (7)

IR (KBr) cm$^{-1}$: 1715, 1652, 1615

$^1$H-NMR (CDCl$_3$) δ: 1.16 (6H, d, J=7 Hz), 1.28 (6H, d, J=7 Hz), 1.40 (3H, t, J=7 Hz), 2.81 (1H, sep, J=7 Hz), 3.06 (1H, sep, J=7 Hz), 4.38 (2H, q, J=7 Hz), 6.32 (1H, d, J=15 Hz), 6.49 (1H, s), 7.35 (1H, br s, NH), 7.42 (1H, dd, J=7.5, 7.5 Hz), 7.45 (1H, d, J=15 Hz), 7.79 (1H, ddd, J=7.5, 1.5, 1 Hz), 8.04 (1H, br ddd, J=7.5, 2, 1 Hz), 8.07 (1H, dd, J=2, 1.5 Hz)

The ester obtained above (76 mg, 0.206 mmol) was hydrolyzed with lithium hydroxide in a conventional manner, and the residue was recrystallized to obtain the title compound (28, 67 mg, 95%) as pale yellow prisms.

Mp: 220.5-221.5° C. (Et$_2$O-hexane)

MS (m/z): 341 (M$^+$, 12), 205 (100), 147 (5), 91 (12), 65 (10), 43 (19), 41 (10)

IR (KBr) cm$^{-1}$: 1687, 1653, 1615

$^1$H-NMR (DMSO-d6) δ: 1.10 (6H, d, J=7 Hz), 1.21 (6H, d, J=7 Hz), 2.80 (1H, sep, J=7 Hz), 3.08 (1H, sep, J=7 Hz), 6.48 (1H, d, J=15 Hz), 6.74 (1H, s), 7.27 (1H, d, J=15 Hz), 7.42 (1H, dd, J=8, 7.5 Hz). 7.60 (1H, ddd, J=7.5, 1.5, 1 Hz), 7.86 (1H, ddd, J=8, 2, 1 Hz), 8.30 (1H, dd, J=2, 1.5 Hz).), 10.33 (1H, br s, NH).

Example 31

3-[[3-(4,5-Diisopropyl-2-furanyl)acryloyl]methylamino]benzoic acid (29)

[Formula 32]

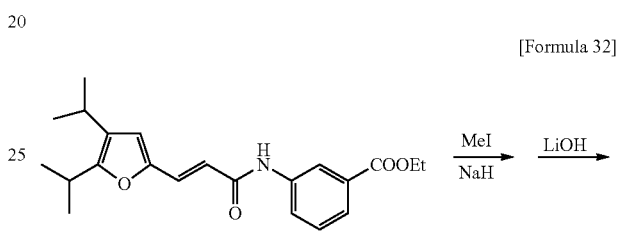

[Formula 31]

-continued

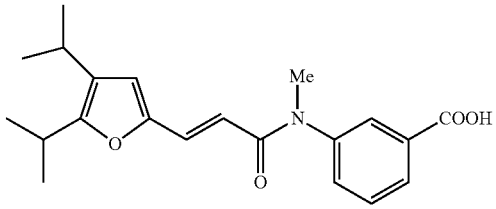

In the same manner as that of Example 29, ethyl 3-[[3-(4,5-diisopropyl-2-furanyl)acryloyl]amino]benzoate (135 mg, 0.366 mmol) was methylated with methyl iodide and sodium hydride, and then the resultant was purified by silica gel chromatography [benzene-ethyl acetate (4:1)] and recrystallized to obtain ethyl 3-[[3-(4,5-diisopropyl-2-furanyl)acryloyl]methylamino]benzoate (123 mg, 88%) as colorless prisms.

Mp: 93-94° C. (CH$_2$Cl$_2$-hexane)
MS (m/z): 383 (M$^+$, 8), 338 (2), 205 (100), 165 (5), 105 (5), 91 (9), 77 (7), 43 (16)
IR (KBr) cm$^{-1}$: 1711, 1645, 1612
$^1$H-NMR (CDCl$_3$) δ: 1.11 (6H, d, J=7 Hz), 1.12 (6H, d, J=7 Hz), 1.40 (3H, t, J=7 Hz), 2.75 (1H, sep, J=7 Hz), 2.94 (1H, sep, J=7 Hz), 3.42 (3H, s), 4.40 (2H, q, J=7 Hz), 6.08 (1H, d, J=15 Hz), 6.37 (1H, s), 7.37 (1H, d, J=15 Hz), 7.41 (1H, ddd, J=7.5, 2, 1.5 Hz), 7.50 (1H, dd, J=7.5, 7.5 Hz), 7.92 (1H, dd, J=2, 1.5 Hz), 8.03 (1H, ddd, J=7.5, 1.5, 1.5 Hz)

This ester (94 mg, 0.245 mmol) was hydrolyzed with lithium hydroxide in a conventional manner, and the residue was recrystallized to obtain the title compound (29, 82 mg, 94%) as colorless prisms.

Mp: 187.5-189° C. (CH$_2$Cl$_2$-hexane)
MS (m/z): 355 (M$^+$, 10), 205 (100), 91 (11), 65 (10), 43 (17), 41 (10)
IR (KBr) cm$^{-1}$: 1711, 1637
$^1$H-NMR (CDCl$_3$) δ: 1.11 (6H, d, J=7 Hz), 1.12 (6H, d, J=7 Hz), 2.75 (1H, sep, J=7 Hz), 2.94 (1H, sep, J=7 Hz), 3.44 (3H, s), 6.09 (1H, d, J=15 Hz), 6.39 (1H, s), 7.40 (1H, d, J=15 Hz), 7.49 (1H, ddd, J=7.5, 2, 1.5 Hz), 7.54 (1H, dd, J=7.5, 7.5 Hz), 8.01 (1H, dd, J=2, 1.5 Hz), 8.10 (1H, ddd, J=7.5, 1.5, 1.5 Hz).

Example 32

5-[(4,5-Diisopropylfuran-2-carbonyl)amino]-2-furancarboxylic acid (35)

[Formula 33]

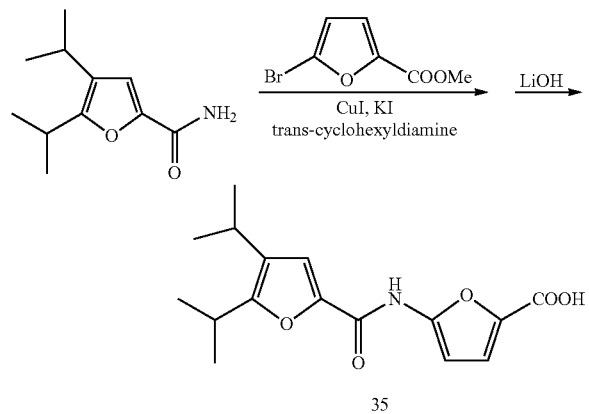

4,5-Diisopropylfuran-2-carboxamide (55 mg, 0.282 mmol) and methyl 5-bromofuran-2-carboxylate (116 mg, 0.566 mmol) were coupled. The reaction mixture was treated in a conventional manner, and the resultant was purified by silica gel chromatography [hexane-ethyl acetate (9:1)] and recrystallized to obtain methyl 5-[(4,5-diisopropylfuran-2-carbonyl)amino]-2-furancarboxylate (44 mg, 49%) and the collected starting material (26 mg, 47%) as colorless needles.

Mp: 169.5-170.5° C. (CH$_2$Cl$_2$-hexane)
MS (m/z): 319 (M$^+$, 9), 288 (2), 204 (2), 179 (100), 91 (8), 80 (9), 53 (6), 43 (6), 40 (7)
IR (KBr) cm$^{-1}$: 1699, 1651
$^1$H-NMR (CDCl$_3$) δ: 1.17 (6H, d, J=7 Hz), 1.30 (6H, d, J=7 Hz), 2.84 (1H, sep, J=7 Hz), 3.11 (1H, sep, J=7 Hz), 3.90 (3H, s), 6.63 (1H, d, J=3.5 Hz), 7.18 (1H, s), 7.23 (1H, d, J=3.5 Hz), 8.72 (1H, br s, NH)

This ester (42 mg, 0.132 mmol) was hydrolyzed with lithium hydroxide in a conventional manner, and then the residue was recrystallized to obtain the title compound (35, 30 mg, 75%) as pale yellow prisms.

Mp: 169-171° C. (CH$_2$Cl$_2$-hexane)
MS (m/z): 305 (M$^+$, 0.1), 261 (12), 179 (100), 108 (6), 81 (7), 55 (8), 44 (10), 43 (15), 41 (15)
IR (KBr) cm$^{-1}$: 1667
$^1$H-NMR (CDCl$_3$) δ: 1.18 (6H, d, J=7 Hz), 1.30 (6H, d, J=7 Hz), 2.84 (1H, sep, J=7 Hz), 3.11 (1H, sep, J=7 Hz), 6.69 (1H, d, J=3.5 Hz), 7.20 (1H, s), 7.38 (1H, d, J=3.5 Hz), 8.71 (1H, br s, NH).

Example 33

5-[(4,5-Diisopropylfuran-2-carbonyl)amino]-2-indolecarboxylic acid (36)

[Formula 34]

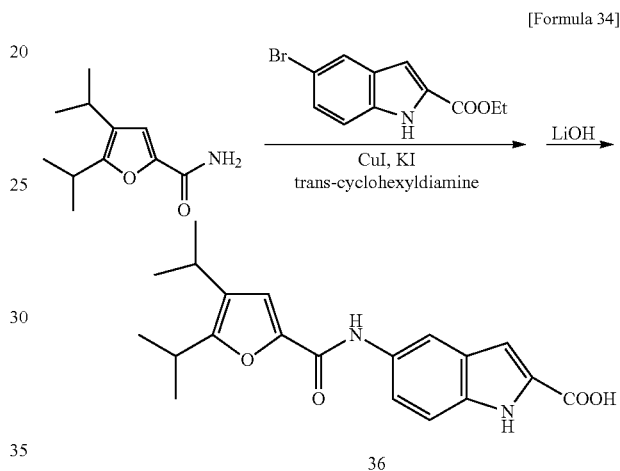

In the same manner as that of Example 32, 4,5-diisopropylfuran-2-carboxamide (71 mg, 0.364 mmol) and ethyl 5-bromoindole-2-carboxylate (195 mg, 0.728 mmol) were coupled. The reaction mixture was treated in a conventional manner, and the resultant was purified by silica gel chromatography [hexane-ethyl acetate (4:1), and 1% methanol-chloroform] and then recrystallized to obtain ethyl 5-[(4,5-diisopropylfuran-2-carbonyl)amino]-2-indolecarboxylate (45 mg, 32%) as colorless prisms, together with the collected starting material (39 mg, 55%).

Mp: 106.5-108° C. (CH$_2$Cl$_2$-hexane)
MS (m/z): 382 (M$^+$, 50), 336 (6), 179 (100), 157 (16), 130 (13), 43 (21), 41 (13)
IR (KBr) cm$^{-1}$: 1689, 1644
$^1$H-NMR (CDCl$_3$) δ: 1.17 (6H, d, J=7 Hz), 1.31 (6H, d, J=7 Hz), 1.41 (3H, t, J=7 Hz), 2.83 (1H, sep, J=7 Hz), 3.11 (1H, sep, J=7 Hz), 4.41 (2H, q, J=7 Hz), 7.15 (1H, s), 7.18 (1H, dd, J=2, 1 Hz), 7.38 (1H, d, J=9 Hz), 7.48 (1H, dd, J=9, 2 Hz), 8.04 (1H, br s, NH), 8.05 (1H, d, J=2 Hz), 9.38 (1H, br s, indole NH)

This ester (38 mg, 99.5 µmol) was hydrolyzed with lithium hydroxide in a conventional manner, and then the residue was recrystallized to obtain the title compound (36, 33 mg, 94%) as colorless prisms.

Mp: 240-243° C. (docomp, CH$_2$Cl$_2$-hexane)
MS (m/z): 354 (M$^+$, 37), 179 (100), 157 (13), 130 (11), 43 (21), 41 (16)
IR (KBr) cm$^{-1}$: 1686
$^1$H-NMR (CDCl$_3$) δ: 1.19 (6H, d, J=7 Hz), 1.33 (6H, d, J=7 Hz), 2.85 (1H, sep, J=7 Hz), 3.12 (1H, sep, J=7 Hz), 7.16 (1H, s), 7.32 (1H, d, J=1.5 Hz), 7.42 (1H, d, J=8.5 Hz), 7.52 (1H, dd, J=8.5, 2 Hz), 7.98 (1H, br s, NH), 8.08 (1H, d, J=2 Hz), 8.96 (1H, br s, indole NH).

Example 34

2-Fluoro-4-[(4,5-diisopropylthiophene-2-carbonyl)amino]benzoic acid (39)

[Formula 35]

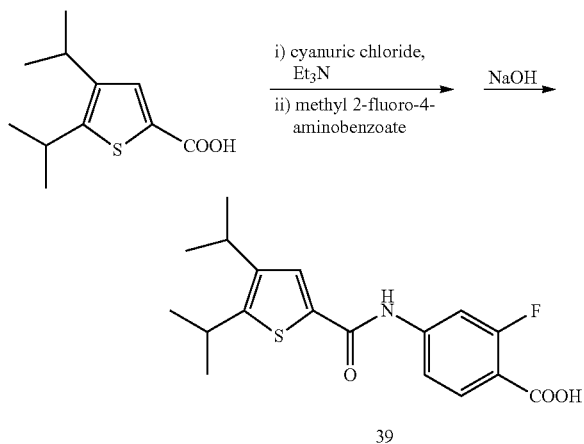

In the same manner as that of Example 24, 4,5-diisopropylthiophene-2-carboxylic acid (80 mg, 0.377 mmol) and methyl 2-fluoro-4-aminobenzoate (115 mg, 0.680 mmol) were condensed, the reaction mixture was treated in a conventional manner, and then the residue was purified by silica gel chromatography [n-hexane-ethyl acetate (40:1)] and recrystallized to obtain methyl 2-fluoro-4-[(4,5-diisopropylthiophene-2-carbonyl)amino]benzoate (45 mg, 33%) as colorless prisms.

Mp: 146-147° C. (CHCl$_3$-hexane)

$^1$H-NMR (CDCl$_3$) δ: 1.22 (6H, d, J=7 Hz), 1.33 (6H, d, J=7 Hz), 3.04 (1H, sep, J=7 Hz), 3.34 (1H, sep, J=7 Hz), 3.92 (3H, s), 7.29 (1H, dd, J=8, 2 Hz), 7.50 (1H, s), 7.71 (1H, dd, J=13, 2 Hz), 7.79 (1H, br s, NH), 7.93 (1H, t, J=8 Hz)

The aforementioned ester (42 mg, 0.116 mmol) was hydrolyzed with sodium hydroxide in a conventional manner, and extraction and recrystallization were performed to obtain the title compound (39, 34 mg, 83%) as colorless prisms.

Mp: 133-135° C. (EtOAc-hexane)

$^1$H-NMR (CDCl$_3$) δ: 1.25 (6H, d, J=7 Hz), 1.34 (6H, d, J=7 Hz), 3.06 (1H, sep, J=7 Hz), 3.35 (1H, sep, J=7 Hz), 7.31 (1H, dd, J=8, 2 Hz), 7.50 (1H, s), 7.73 (1H, br s, NH), 7.77 (1H, dd, J=13, 2 Hz), 8.01 (1H, t, J=8 Hz)

Example 35

2-Chloro-4-[(4,5-diisopropylthiophene-2-carbonyl)amino]benzoic acid (40)

[Formula 36]

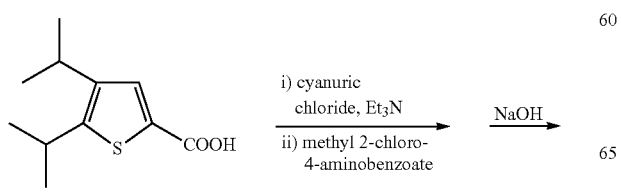

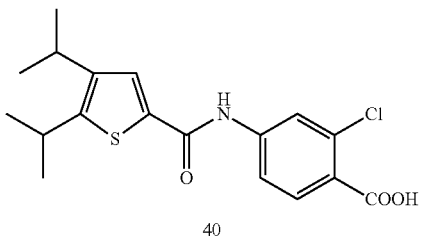

In the same manner as that of Example 24, 4,5-diisopropylthiophene-2-carboxylic acid (80 mg, 0.377 mmol) and methyl 2-chloro-4-aminobenzoate (126 mg, 0.679 mmol) were condensed, the reaction mixture was treated in a conventional manner, and then the residue was purified by silica gel chromatography [n-hexane-ethyl acetate (40:1)] and recrystallized to obtain methyl 2-chloro-4-[(4,5-diisopropylthiophene-2-carbonyl)amino]benzoate (49 mg, 34%) as colorless prisms.

Mp: 153-154° C. (CHCl$_3$-hexane)

$^1$H-NMR (CDCl$_3$) δ: 1.23 (6H, d, J=7 Hz), 1.33 (6H, d, J=7 Hz), 3.05 (1H, sep, J=7 Hz), 3.34 (1H, sep, J=7 Hz), 3.92 (3H, s), 7.49 (1H, s), 7.62 (1H, dd, J=9, 2 Hz), 7.71 (1H, br s, NH), 7.89 (1H, d, J=2 Hz), 7.90 (1H, d, J=9 Hz)

The aforementioned ester (46 mg, 0.121 mmol) was hydrolyzed with sodium hydroxide in a conventional manner, and extraction and recrystallization were performed to obtain the title compound (40, 40 mg, 91%) as colorless prisms.

Mp: 222-223° C. (EtOAc-hexane)

$^1$H-NMR (CDCl$_3$) δ: 1.25 (6H, d, J=7 Hz), 1.34 (6H, d, J=7 Hz), 3.06 (1H, sep, J=7 Hz), 3.35 (1H, sep, J=7 Hz), 7.50 (1H, s), 7.63 (1H, dd, J=9, 2 Hz), 7.66 (1H, br s, NH), 7.85 (1H, d, J=2 Hz), 8.06 (1H, d, J=9 Hz)

Example 36

2-Hydroxy-4-[(4,5-diisopropylthiophene-2-carbonyl)amino]benzoic acid (41)

[Formula 37]

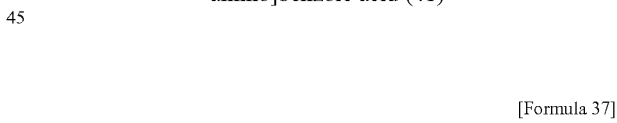

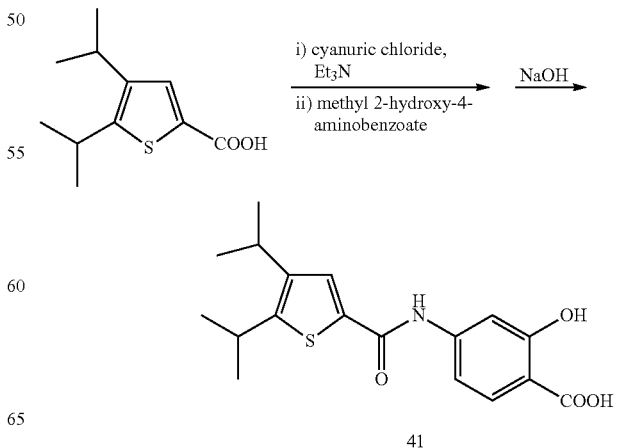

In the same manner as that of Example 24, 4,5-diisopropylthiophene-2-carboxylic acid (80 mg, 0.377 mmol) and methyl 2-hydroxy-4-aminobenzoate (113 mg, 0.676 mmol) were condensed, the reaction mixture was treated in a conventional manner, and then the residue was purified by silica gel chromatography [n-hexane-ethyl acetate (40:1)] and recrystallized to obtain methyl 2-hydroxy-4-[(4,5-diisopropylthiophene-2-carbonyl)amino]benzoate (45 mg, 33%) as colorless prisms.

Mp: 180-181° C. (CHCl$_3$-hexane)

$^1$H-NMR (CDCl$_3$) δ: 1.23 (6H, d, J=7 Hz), 1.33 (6H, d, J=7 Hz), 3.04 (1H, sep, J=7 Hz), 3.33 (1H, sep, J=7 Hz), 3.93 (3H, s), 7.21 (1H, dd, J=9, 2 Hz), 7.26 (1H, d, J=2 Hz), 7.48 (1H, s), 7.68 (1H, br s, NH), 7.80 (1H, d, J=9 Hz), 10.86 (1H, s, OH)

The aforementioned ester (42 mg, 0.116 mmol) was hydrolyzed with sodium hydroxide in a conventional manner, and extraction and recrystallization were performed to obtain the title compound (41, 29 mg, 73%) as colorless prisms.

Mp: 129-130° C. (MeOH—CHCl$_3$-hexane)

$^1$H-NMR (CDCl$_3$) δ: 1.24 (6H, d, J=7 Hz), 1.33 (6H, d, J=7 Hz), 3.05 (1H, sep, J=7 Hz), 3.34 (1H, sep, J=7 Hz), 7.19 (1H, dd, J=9, 2 Hz), 7.35 (1H, d, J=2Hz), 7.50 (1H, s), 7.68 (1H, br s, NH), 7.89 (1H, d, J=9 Hz), 10.52 (1H, br s, OH)

Example 37

2-Methoxy-4-[(4,5-diisopropylthiophene-2-carbonyl)amino]benzoic acid (42)

[Formula 38]

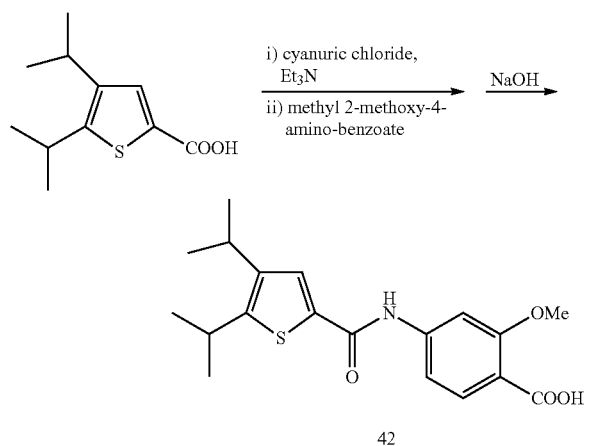

In the same manner as that of Example 24, 4,5-diisopropylthiophene-2-carboxylic acid (80 mg, 0.377 mmol) and methyl 2-methoxy-4-aminobenzoate (123 mg, 0.679 mmol) were condensed, the reaction mixture was treated in a conventional manner, and then the residue was purified by silica gel chromatography [n-hexane-ethyl acetate (40:1)] and recrystallized to obtain methyl 2-methoxy-4-[(4,5-diisopropylthiophene-2-carbonyl)amino]benzoate (46 mg, 32%) as colorless prisms.

Mp: 172-173° C. (CHCl$_3$-hexane)

$^1$H-NMR (CDCl$_3$) δ: 1.23 (6H, d, J=7 Hz), 1.33 (6H, d, J=7 Hz), 3.05 (1H, sep, J=7 Hz), 3.34 (1H, sep, J=7 Hz), 3.88 (3H, s), 3.94 (3H, s), 6.93 (1H, dd, J=8, 2 Hz), 7.50 (1H, s), 7.75 (1H, br s, NH), 7.77 (1H, d, J=2 Hz), 7.85 (1H, d, J=9 Hz)

The aforementioned ester (42 mg, 0.112 mmol) was hydrolyzed with sodium hydroxide in a conventional manner, and extraction and recrystallization were performed to obtain the title compound (42, 35 mg, 88%) as colorless needles.

Mp: 213-214° C. (MeOH—CHCl$_3$)

$^1$H-NMR (CDCl$_3$) δ: 1.25 (6H, d, J=7 Hz), 1.34 (6H, d, J=7 Hz), 3.06 (1H, sep, J=7 Hz), 3.35 (1H, sep, J=7 Hz), 4.12 (3H, s), 6.88 (1H, dd, J=8, 2 Hz), 7.51 (1H, s), 7.79 (1H, br s, NH), 8.14 (1H, d, J=2 Hz), 8.14 (1H, d, J=8 Hz)

Example 38

2,6-Difluoro-4-[(4,5-diisopropylthiophene-2-carbonyl)amino]benzoic acid (43)

[Formula 39]

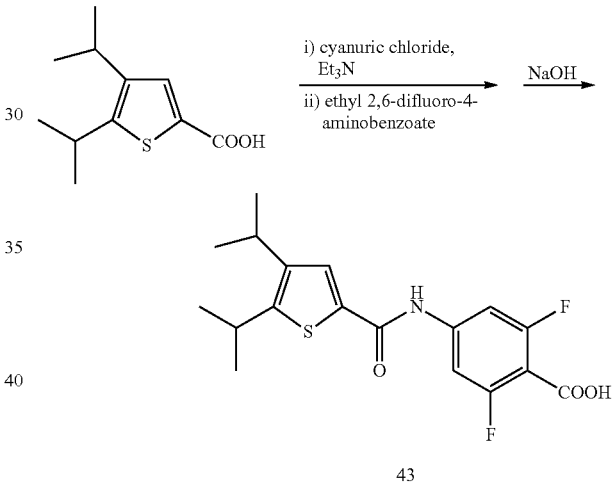

In the same manner as that of Example 24, 4,5-diisopropylthiophene-2-carboxylic acid (80 mg, 0.377 mmol) and ethyl 2,6-difluoro-4-aminobenzoate (137 mg, 0.681 mmol) were condensed, the reaction mixture was treated in a conventional manner, and then the residue was purified by silica gel chromatography [n-hexane-ethyl acetate (40:1)] to obtain methyl 2,6-difluoro-4-[(4,5-diisopropylthiophene-2-carbonyl)amino]benzoate (88 mg, 59%).

$^1$H-NMR (CDCl$_3$) δ: 1.22 (6H, d, J=7 Hz), 1.32 (6H, d, J=7 Hz), 1.38 (3H, t, J=7 Hz), 3.04 (1H, sep, J=7 Hz), 3.33 (1H, sep, J=7 Hz), 4.39 (2H, q, J=7 Hz), 7.33 (2H, d, J=10 Hz), 7.50 (1H, s), 7.92 (1H, br s, NH)

The aforementioned ester (83 mg, 0.209 mmol) was hydrolyzed with sodium hydroxide in a conventional manner, and extraction and recrystallization were performed to obtain the title compound (43, 66 mg, 86%) as colorless prisms.

Mp: 218-219° C. (EtOAc-hexane)

$^1$H-NMR (CDCl$_3$) δ: 1.24 (6H, d, J=7 Hz), 1.33 (6H, d, J=7 Hz), 3.05 (1H, sep, J=7 Hz), 3.34 (1H, sep, J=7 Hz), 7.36 (1H, d, J=11 Hz), 7.51 (1H, s), 7.80 (1H, br s, NH)

Example 39

4-[[3-(4,5-Diisopropyl-2-thiophene)acryloyl]amino]benzoic acid (44)

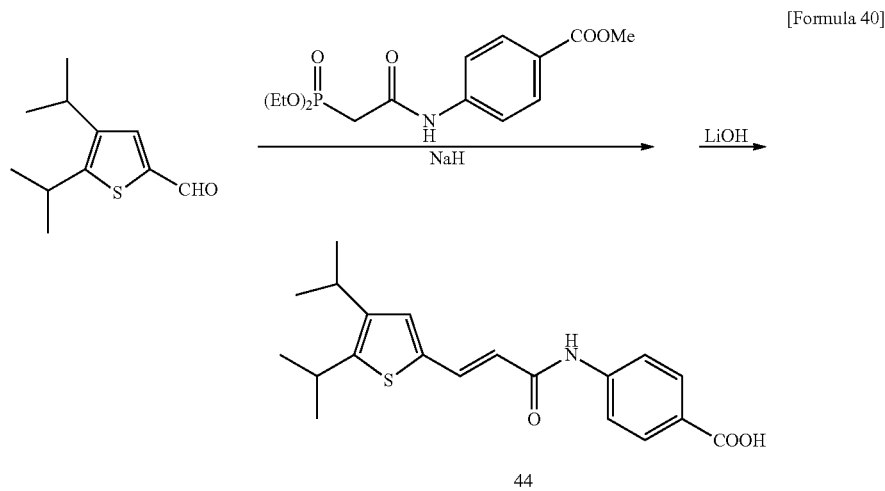

In the same manner as that of Example 13, methyl 4-[(diethoxyphosphoryl)acetamino]benzoate (428 mg, 1.30 mmol) and sodium hydride (60% mineral oil dispersion, 52 mg, 1.30 mmol) were allowed to act on 4,5-diisopropylthiophene-2-aldehyde (170 mg, 0.867 mmol), the reaction mixture was treated in a conventional manner, and then the resultant was purified by silica gel chromatography [benzene-ethyl acetate (24:1)] and recrystallized to obtain methyl 4-[[3-(4,5-diisopropyl-2-thiophene)acryloyl]amino]benzoate (296 mg, 92%) was pale yellow prisms.

Mp: 162.5-163.5° C. (Et$_2$O-hexane)

MS (m/z): 371 (M$^+$, 13), 340 (1), 221 (100), 163 (5), 120 (4), 91 (5), 43 (5)

IR (KBr) cm$^{-1}$: 1685

$^1$H-NMR (CDCl$_3$) δ: 1.21 (6H, d, J=7 Hz), 1.30 (6H, d, J=7 Hz), 3.00 (1H, sep, J=7 Hz), 3.31 (1H, sep, J=7 Hz), 3.91 (3H, s), 6.21 (1H, d J=15 Hz), 7.07 (1H, s), 7.39 (1H, br s, NH), 7.69 (2H, A$_2$B$_2$, J=8.5 Hz), 7.81 (1H, d, J=15 Hz), 8.03 (2H, A$_2$B$_2$, J=8.5 Hz), The aforementioned ester (92 mg, 0.248 mmol) was hydrolyzed with lithium hydroxide in a conventional manner, and extraction and recrystallization were performed to obtain the title compound (44, 84 mg, 95%) was pale yellow prisms.

Mp: 241.5-244° C. (CH$_2$Cl$_2$)

MS (m/z): 357 (M$^+$, 11), 221 (100), 163 (7), 149 (5), 91 (5), 65 (6), 43 (7)

IR (KBr) cm$^{-1}$: 1684, 1600. $^1$H-NMR (DMSO-d$_6$) δ: 1.13 (6H, d, J=6.5 Hz), 1.22 (6H, d, J=6.5 Hz), 2.97 (1H, sep, J=6.5 Hz), 3.29 (1H, sep, J=6.5 Hz), 6.42 (1H, d J=15 Hz), 7.28 (1H, s), 7.63 (1H, d, J=15 Hz), 7.74 (2H, A$_2$B$_2$, J=8.5 Hz), 7.87 (2H, A$_2$B$_2$, J=8.5 Hz), 10.42 (1H, br s, NH)

Test Example 1

Cells of human acute promyelocytic leukemia cell strain HL-60 were cultured in a CO$_2$ incubator (5% CO$_2$, 37° C.) using the RPMI medium containing 5% FBS. Differentiation inducing action of the compounds of the present invention on the HL-60 cells were evaluated on the basis of ability to reduce nitroblue tetrazolium (NBT) determined by observing differentiation from promyelocytic cells into granulocytic cells as an index. As positive control of retinoid compounds, retinoic acid and Am80 [4-[(5,6,7,8-tetrahydro-5,5,8,8-tetramethyl-2-naphthalenyl)carbamoyl]benzoic acid] were used. The cells that entered into the logarithmic phase and reached a substantially confluent state were centrifuged at 1000 rpm for 5 minutes, and the culture supernatant was removed. The cell pellet was suspended in fresh RPMI medium containing 5% FBS at a density of 8.0×10$^4$ cells/ml, then the suspension was added with a test compound dissolved in DMSO at an intended concentration, and the cells were cultured for four days and then used for the experiment. The samples were prepared so as to have the same DMSO concentration.

Cell count of the cells after the culture for a predetermined period was determined by a cell counting method using a blood cell counting chamber. The NBT-reducing ability was obtained as follows. NBT was dissolved in a phosphate buffered saline (PBS(−)) at a concentration of 0.2%, and the solution was added with an equivalent volume of the RPMI medium containing 5% FBS. The mixture was added with phorbol 12-myristate 13-acetate (tPA) at a concentration of 0.2 μM (about 200 ng) to prepare a reagent solution. The collected cells were centrifuged at 1000 rpm for 5 minutes, the supernatant was removed, and the remained cell pellet was added with the reagent solution. The mixture was incubated on a water bath at 37° C. for 20 minutes, and then NBT-reduced stained positive cells were counted by using the counting chamber to calculate a differentiation induction ratio.

The results are shown in Table 1. It was demonstrated that the compounds of the present invention had a differentiation-inducing action comparable to that of Am80. The differentiation induction ratios of 4-[(5-t-butylfuran-2-carbonyl)amino]benzoic acid and 4-[(5-t-butylthiophene-2-carbonyl)amino]benzoic acid, which are compounds of the general formula (I) wherein $R^2$ is hydrogen atom, are described in the literature (Pharmacology & Toxicology, 85, 49-55, 1999), and it is known that 4-[(5-t-butylfuran-2-carbonyl)amino]benzoic acid shows differentiation induction ratios of 60% at 74 μM, 42% at 19 μM, and 26% at 3.7 μM, and 4-[(5-t-butylthiophene-2-carbonyl)amino]benzoic acid shows differentiation induction ratios of 23% at 5.6 μM, and 22% at 1.1 μM, and no differentiation induction at 0.22 μM. Therefore, the compounds of the present invention have differentiation-inducing action much higher than that of the aforementioned compounds of the general formula (I) wherein $R^2$ is hydrogen atom, and it is considered that the alkyl group introduced as $R^2$ is responsible for this potent action.

TABLE 1

| No | $ED_{50}$ [nM] | Differentiation induction ratio (%) | |
|---|---|---|---|
| | | $1 \times 10^{-8}$M | $1 \times 10^{-7}$M |
| 1 | 1.1 | 45.3 | 45.2 |
| 3 | ND | 4.9 | 5.8 |
| 5 | ND | 7.0 | 6.1 |
| 6 | >1,000 | 4.2 | 9.3 |
| 7 | 13.1 | 7.5 | 43.5 |
| 8 | 1.9 | 65.1 | 68.6 |
| 9 | 72.9 | 7.7 | 39.8 |
| 10 | 166.3 | 10.2 | 31.6 |
| 11 | 74.7 | 6.9 | 41.5 |
| 12 | 40.4 | 8.3 | 39.1 |
| 13 | ND | 3.7 | 2.6 |
| 14 | >1,000 | 2.4 | 5.9 |
| 15 | 1.8 | 53.3 | 57.1 |
| Am80 | 1.6 | 66-78 | 65-78 |

INDUSTRIAL APPLICABILITY

The compound of the present invention, a salt thereof, and an ester thereof have a retinoid action, and can be used as a medicament for prophylactic and/or therapeutic treatment for various kinds of diseases which can be prevented and/or cured with a retinoid such as retinoic acid.

What is claimed is:

1. A compound represented by the following formula (I):

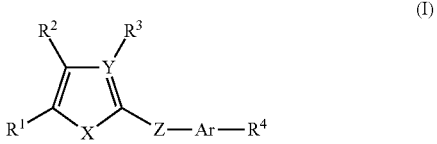

[wherein $R^1$ and $R^2$ independently represent a $C_{3-10}$ alkyl group (the alkyl group may have a substituent selected from halogen atom, hydroxyl group, alkoxy group, amino group, and oxo group), X represents —O—, Y represents C, $R^3$ represents hydrogen atom or a $C_{1-10}$ alkyl group (the alkyl group may have a substituent selected from halogen atom, hydroxyl group, alkoxy group, amino group, and oxo group), Z represents —CO—N($R^5$)— ($R^5$ represents hydrogen atom or a $C_{1-6}$ alkyl group) or —C($R^6$)=C($R^7$)—CO—NH— ($R^6$ and $R^7$ independently represent hydrogen atom or a $C_{1-6}$ alkyl group), Ar represents an aryldiyl group (the aryldiyl group may have a substituent selected from halogen atom, hydroxyl group, alkoxy group, and alkyl group), and $R^4$ represents —COOH, —OCH$_2$—COOH, —CH$_2$—COOH, or —CH$_2$—CH$_2$—COOH], or a salt thereof.

2. The compound or salt thereof according to claim 1, wherein $R^1$ and $R^2$ represent isopropyl group, X is —O—, Y is C, $R^3$ is hydrogen atom or a $C_{1-10}$ alkyl group, Z is —CO—NH—, —CH=CH—CO—NH—, or —C(CH$_3$)=CH—CO—NH—, Ar is a phenylene group, and $R^4$ is —COOH, —OCH$_2$—COOH, —CH$_2$—COOH, or —CH$_2$—CH$_2$—COOH.

3. The compound or salt thereof according to claim 1, wherein $R^1$ and $R^2$ represent isopropyl group, X is —O—, Y is C, $R^3$ is hydrogen atom, Z is —CO—NH—, Ar is a phenylene group, and $R^4$ is —COOH.

4. A pharmaceutical composition comprising a pharmaceutically acceptable additive and the compound according to claim 1 or a physiologically acceptable salt thereof as an active ingredient.

5. A pharmaceutical composition comprising a pharmaceutically acceptable additive and the compound according to claim 2 or a physiologically acceptable salt thereof as an active ingredient.

6. A pharmaceutical composition comprising a pharmaceutically acceptable additive and the compound according to claim 3 or a physiologically acceptable salt thereof as an active ingredient.

* * * * *